United States Patent
Ko et al.

(10) Patent No.: US 10,273,458 B2
(45) Date of Patent: Apr. 30, 2019

(54) ZSCAN4 AS A MARKER FOR PANCREATIC STEM CELLS AND PROGENITOR CELLS AND USE THEREOF

(75) Inventors: Minoru S. H. Ko, Cockeysville, MD (US); Shigeru B. H. Ko, Inuyama (JP)

(73) Assignee: Elixirgen, LLC, Baltimore, MD (US)

( * ) Notice: Subject to any disclaimer, the term of this patent is extended or adjusted under 35 U.S.C. 154(b) by 561 days.

(21) Appl. No.: 13/981,891

(22) PCT Filed: Jan. 25, 2012

(86) PCT No.: PCT/US2012/022575
§ 371 (c)(1),
(2), (4) Date: Oct. 22, 2013

(87) PCT Pub. No.: WO2012/103235
PCT Pub. Date: Aug. 2, 2012

(65) Prior Publication Data
US 2014/0065193 A1     Mar. 6, 2014

Related U.S. Application Data

(60) Provisional application No. 61/436,068, filed on Jan. 25, 2011.

(51) Int. Cl.
| | |
|---|---|
| C12N 5/00 | (2006.01) |
| C12N 15/63 | (2006.01) |
| C12N 5/071 | (2010.01) |
| G01N 33/50 | (2006.01) |
| G01N 33/68 | (2006.01) |
| A61K 35/39 | (2015.01) |
| A61K 38/17 | (2006.01) |
| C12Q 1/6897 | (2018.01) |
| G01N 33/569 | (2006.01) |
| A61K 48/00 | (2006.01) |

(52) U.S. Cl.
CPC ........... *C12N 5/0678* (2013.01); *A61K 35/39* (2013.01); *A61K 38/1709* (2013.01); *C12Q 1/6897* (2013.01); *G01N 33/507* (2013.01); *G01N 33/5073* (2013.01); *G01N 33/56966* (2013.01); *G01N 33/6893* (2013.01); *G01N 2800/042* (2013.01)

(58) Field of Classification Search
CPC .. C12N 5/0678; A61K 38/1709; A61K 35/39; G01N 33/56966; G01N 33/6893; G01N 33/5073; G01N 33/507; G01N 2800/042; C12Q 1/6897
See application file for complete search history.

(56) References Cited

U.S. PATENT DOCUMENTS

| | | |
|---|---|---|
| 2004/0058457 A1 | 3/2004 | Huang et al. |
| 2005/0277190 A1 | 12/2005 | Seaberg et al. |
| 2006/0251642 A1 | 11/2006 | Wolffe et al. |

FOREIGN PATENT DOCUMENTS

| | | |
|---|---|---|
| JP | 2003523323 | 8/2003 |
| JP | 2010522565 | 7/2010 |
| WO | WO-2001039784 | 6/2001 |
| WO | 2005/033126 A1 | 4/2005 |
| WO | WO-2005070413 | 8/2005 |
| WO | WO-2008/118957 A2 | 10/2008 |
| WO | WO-2008118957 | 10/2008 |
| WO | WO-2011/028880 A2 | 3/2011 |

OTHER PUBLICATIONS

Zhang et al 2006, Nucleic Acids Research 34:4780-4790.*
And Stickings et al 2002, Nitric Oxide 7:289-296.*
Lee et al 1997, Genomics 43:191-207.*
International Search Report dated May 29, 2012, for PCT/US12/22575, 3 pages.
Pi et al. (2002). "A novel human SCAN/(Cys)2(His)2 zinc-finger transcription factor ZNF323 in early human embryonic development," Biochem and Biophys Res Comm 296:206-213.
Zalzman et al. (2010). "Zscan4 regulates telomere elongation and genomic stability in ES cells," Nature 464:858-863.
Zhang et al. (2006). "Zfp206 regulates ES cell gene expression and differentiation," Nucleic Acids Res 34:4780-4790.
Extended European Search Report (includes Supplementary European Search Report and Search Opinion) received for European Patent Application No. 12738829.6, dated Aug. 5, 2014, 6 pages.
International Preliminary Report on Patentability received for PCT Patent Application No. PCT/US2012/022575, dated Aug. 8, 2013, 8 pages.

(Continued)

*Primary Examiner* — Quang Nguyen
(74) *Attorney, Agent, or Firm* — Morrison & Foerster LLP

(57) ABSTRACT

ZSCAN4, a gene expressed in ES cells and 2-cell stage embryos, has been previously shown to regulate telomere elongation and genome stability in mouse ES cells. It is disclosed herein that in the adult human pancreas, a small number of ZSCAN4-positive cells are present among cells located in the islets of Langerhans, acini, and ducts. These data disclosed herein indicates that expression of ZSCAN4 is a marker for rare stem/progenitor cells in adult human pancreas. Thus, provided herein is a method of isolating pancreatic stem cells or progenitor cell from a sample by detecting expression of ZSCAN4. Also provided is a method of treating diabetes by isolating ZSCAN4$^+$ pancreatic stem cells or progenitor cells, expanding the cells in vitro and transplanted the expanded cells into the subject. The expanded ZSCAN4$^+$ cells can optionally be differentiated into pancreatic β cells before transplanting the cells into the subject. Further provided is an in vivo method of expanding a population of pancreatic stem cells or progenitor cells in a subject by delivering a ZSCAN4 protein, a ZSCAN4 nucleic acid sequence, or an agent that increases expression of ZSCAN4 to the pancreas of the subject.

16 Claims, 11 Drawing Sheets
(8 of 11 Drawing Sheet(s) Filed in Color)
Specification includes a Sequence Listing.

(56) References Cited

OTHER PUBLICATIONS

Written Opinion received for PCT Patent Application No. PCT/US2012/022575, dated May 29, 2012, 6 pages.
Rovira et al., "Isolation and Characterization of Centroacinar/Terminal Ductal Progenitor Cells in Adult Mouse Pancreas", Proceedings of the National Academy of Sciences of the United States of America, vol. 107, No. 1, Jan. 5, 2010, pp. 75-80.
Ko et al., "Inflammation Increases Cells Expressing ZSCAN4 and Progenitor Cell Markers in the Adult Pancreas", American Journal of Physiology Gastrointestinal and Liver Physiology, vol. 304, 2013, pp. G1103-G1116.

* cited by examiner

SEQUENCE LISTING

```
<160> NUMBER OF SEQ ID NOS: 15

<210> SEQ ID NO 1
<211> LENGTH: 2230
<212> TYPE: DNA
<213> ORGANISM: Homo sapiens

<400> SEQUENCE: 1
ccttgtaatt cataaatctc tgaaaactta aaagtttgag caaaagtttg tcatgtttct      60
atgagtaatt tataataaaa cttgatcaga atttgtgaga ctagcgtttg tctttatatt    120 ttccttttt tttttttttt tttgagacac agtctcgctc tgtcgtccag gctggagtgc    180
cgtggcgtaa tctcggctca ctgcaacctc tgcctcctgg attcaaacaa ttcttctgcc    240
tcagcctcct gagtagctgg gattacagga ccagtgatgg tatagaacac tgtattagag    300
acatggagct ggggctggat gaagattcca tcagtaattc aatcaacaga caagtgttat    360
```

| | |
|---|---|
| ccaatcacgt ctttaaatca atcactgaca tggagctggg gctggatgaa gattccatca | 420 |
| gtaattcaat caacagacaa gtgttatcca atcacgtctt taaatcaatc actgatccca | 480 |
| gccctataa aagggagcag ccttaggagg cacatcagat aaacccagtg tggaaagcta | 540 |
| gtcacacatc agctcagtgt tcggcccggg attacccagt caaccaagga gcttgcagtt | 600 |
| ttaaagaatc caccaactgt tgaaacaaat ccctagagac acaaggcaag agactgaatc | 660 |
| atcaaagtaa agtctctctg agaattattg ctaagaatgg ctttagatct aagaaccata | 720 |
| tttcagtgtg aaccatccga gaataatctt ggatcagaaa attcagcgtt tcaacaaagc | 780 |
| caaggacctg ctgttcagag agaagaaggg atttctgagt tctcaagaat ggtgctcaat | 840 |
| tcatttcaag acagcaataa ttcatatgca aggcaggaat tgcaaagact ttataggatc | 900 |
| tttcactcat ggctgcaacc agaaaagcac agcaaggatg aaattatttc tctattagtc | 960 |
| ctggagcagt ttatgattgg tggccactgc aatgacaaag ccagtgtgaa agagaaatgg | 1020 |
| aaatcaagtg gcaaaaactt ggagagattc atagaagacc tgactgatga cagcataaat | 1080 |
| ccacctgcct tagtccacgt ccacatgcag ggacaggaag ctctcttttc tgaggatatg | 1140 |
| cccttaagag atgtcattgt tcatctcaca aaacaagtga atgcccaaac cacaagagaa | 1200 |
| gcaaacatgg ggacaccctc ccagacttcc caagatactt ccttagaaac aggacaagga | 1260 |
| tatgaagatg aacaagatgg ctggaacagt tcttcgaaaa ctactcgagt aaatgaaaat | 1320 |
| attactaatc aaggcaatca aatagtttcc ctaatcatca tccaggaaga gaacggtcct | 1380 |
| aggcctgaag agggaggtgt ttcttctgac aacccataca actcaaaaag agcagagcta | 1440 |
| gtcactgcta gatctcagga agggtccata aatggaatca ctttccaagg tgtccctatg | 1500 |
| gtgatgggag cagggtgtat ctctcaacca gagcagtcct ccctgagtc tgcccttacc | 1560 |
| caccagagca atgagggaaa ttccacatgt gaggtacatc agaaaggatc ccatggagtc | 1620 |
| caaaaatcat acaaatgtga agaatgcccc aaggtcttta gtatctctg tcacttatta | 1680 |
| gctcaccaga agacacag gaatgagagg ccatttgttt gtcccgagtg tcaaaaaggc | 1740 |
| ttcttccaga tatcagacct acgggtgcat cagataattc acacaggaaa gaagcctttc | 1800 |
| acatgcagca tgtgtaaaaa gtccttcagc cacaaaacca acctgcggtc tcatgagaga | 1860 |
| atccacacag gagaaaagcc ttatacatgt ccctttgta agacaagcta ccgccagtca | 1920 |
| tccacatacc accgccatat gaggactcat gagaaaatta ccctgccaag tgttccctcc | 1980 |
| acaccagaag cttcctaagc tgctggtctg ataatgtgta taaatatgta tgcaagtatg | 2040 |
| tatattccta tagtatttat ctacttagga tataagagat aatctcctga ttatgctttc | 2100 |
| aatttattgt cttgcttcat taaaatgtaa ggctaaggag agcatggaat tgtcagtttt | 2160 |
| tgttcactaa agtattccaa gtggttggga aagtggaaca tttccaagaa ccaataaatt | 2220 |
| tctgttgaat | 2230 |

<210> SEQ ID NO 2
<211> LENGTH: 433
<212> TYPE: PRT
<213> ORGANISM: Homo sapiens

<400> SEQUENCE: 2

Met Ala Leu Asp Leu Arg Thr Ile Phe Gln Cys Glu Pro Ser Glu Asn
1               5                   10                  15

Asn Leu Gly Ser Glu Asn Ser Ala Phe Gln Gln Ser Gln Gly Pro Ala
            20                  25                  30

Val Gln Arg Glu Glu Gly Ile Ser Glu Phe Ser Arg Met Val Leu Asn

```
                35                  40                  45
Ser Phe Gln Asp Ser Asn Asn Ser Tyr Ala Arg Gln Glu Leu Gln Arg
 50                  55                  60

Leu Tyr Arg Ile Phe His Ser Trp Leu Gln Pro Glu Lys His Ser Lys
 65                  70                  75                  80

Asp Glu Ile Ile Ser Leu Leu Val Leu Glu Gln Phe Met Ile Gly Gly
                 85                  90                  95

His Cys Asn Asp Lys Ala Ser Val Lys Glu Lys Trp Lys Ser Ser Gly
                100                 105                 110

Lys Asn Leu Glu Arg Phe Ile Glu Asp Leu Thr Asp Asp Ser Ile Asn
            115                 120                 125

Pro Pro Ala Leu Val His Val His Met Gln Gly Gln Glu Ala Leu Phe
130                 135                 140

Ser Glu Asp Met Pro Leu Arg Asp Val Ile Val His Leu Thr Lys Gln
145                 150                 155                 160

Val Asn Ala Gln Thr Thr Arg Glu Ala Asn Met Gly Thr Pro Ser Gln
                165                 170                 175

Thr Ser Gln Asp Thr Ser Leu Glu Thr Gly Gln Gly Tyr Glu Asp Glu
            180                 185                 190

Gln Asp Gly Trp Asn Ser Ser Lys Thr Thr Arg Val Asn Glu Asn
        195                 200                 205

Ile Thr Asn Gln Gly Asn Gln Ile Val Ser Leu Ile Ile Ile Gln Glu
210                 215                 220

Glu Asn Gly Pro Arg Pro Glu Glu Gly Val Ser Ser Asp Asn Pro
225                 230                 235                 240

Tyr Asn Ser Lys Arg Ala Glu Leu Val Thr Ala Arg Ser Gln Glu Gly
                245                 250                 255

Ser Ile Asn Gly Ile Thr Phe Gln Gly Val Pro Met Val Met Gly Ala
            260                 265                 270

Gly Cys Ile Ser Gln Pro Glu Gln Ser Ser Pro Glu Ser Ala Leu Thr
        275                 280                 285

His Gln Ser Asn Glu Gly Asn Ser Thr Cys Glu Val His Gln Lys Gly
290                 295                 300

Ser His Gly Val Gln Lys Ser Tyr Lys Cys Glu Cys Pro Lys Val
305                 310                 315                 320

Phe Lys Tyr Leu Cys His Leu Leu Ala His Gln Arg His Arg Asn
                325                 330                 335

Glu Arg Pro Phe Val Cys Pro Glu Cys Gln Lys Gly Phe Phe Gln Ile
            340                 345                 350

Ser Asp Leu Arg Val His Gln Ile Ile His Thr Gly Lys Lys Pro Phe
355                 360                 365

Thr Cys Ser Met Cys Lys Lys Ser Phe Ser His Lys Thr Asn Leu Arg
370                 375                 380

Ser His Glu Arg Ile His Thr Gly Glu Lys Pro Tyr Thr Cys Pro Phe
385                 390                 395                 400

Cys Lys Thr Ser Tyr Arg Gln Ser Ser Thr Tyr His Arg His Met Arg
                405                 410                 415

Thr His Glu Lys Ile Thr Leu Pro Ser Val Pro Ser Thr Pro Glu Ala
            420                 425                 430

Ser

<210> SEQ ID NO 3
<211> LENGTH: 2275
```

```
<212> TYPE: DNA
<213> ORGANISM: Mus musculus

<400> SEQUENCE: 3
cacagtgcct ccctgggctt cttggcatca cccttgaagt tcactggaga aagagttgag      60
gtggaggaat aggtaaactt cccttcctag tggtcttgaa tgtctttttac agtacatcca     120
tcaactgtta gcattttcgt aaagtcacaa aacagatatt aaactactat agttgaatct     180
ttcacaccat tgtcaccaca atggcttcac agcaggcacc agcaaaagac cttcagacca     240
acaatttaga gtttactcca actgatagtt ctggtgtgca gtgggcagaa gacatctcta     300
actcaccaag tgctcagcta aacttttccc caagtaacaa tggctgctgg gcaactcagg     360
agctgcaaag tctctggaag atgttcaact cctggttgca gccagaaaag cagactaagg     420
agcagatgat ttctcaactg gtcttggagc agtttctcct cactgggcac tgcaaggaca     480
agtatgcttt gacagagaag tggaaagcca gtggtagcga tatgaggaga ttcatggaga     540
gtctgactga tgagtgcttg aagcctcctg tcatggtcca tgtctcaatg caaggacaag     600
aagccctctt ttctgaaaac atgccattaa agaagtcat caagctttg aaacaacagc     660
aatctgcaac aaggccaaca ccagataatg cacagatgcc agtagacacc acacaagata     720
gattattggc cacaggacaa gaaaacagtg aaaatgaatg caacacctct tgtaatgcta     780
ctgaaggaaa tgttggtgag agctgtagtg gaaatgaaat ggactcctct cttattatcc     840
agaaagaaca gtaccctgag catgaagagg ggaatgttgt ttgtcaattc cctcttgatg     900
ccagaagagc aagtcaaggc acctccagtc atcatgtaga cttcctgagt gctctgacta     960
ctgccgatgt ccccatggag gaacaaccaa aggatttatc cagagaaaac atctctgagg    1020
acaagaacaa ttgctataac acttccagga atgcagctac taaagtatat agtggtgata    1080
atattcccag gaaaaagaca gactcccttt ccattaacaa gaggatatat catcctgagc    1140
ctgaggtggg agatattcct tatggagttc ctcaggattc tacaagagca agtcaaggaa    1200
catctacatg cctgcaagag tcacttgggg gatgtttttc cgaaaaagac cctagggagg    1260
taccagggtt gcagtctagg taagagcagc ctatctctga tcctgtcctt cttggtaaga    1320
atcatgaggc aaacttacca tgtgaaagtc atcaaaagag attctgtaga gatgccaaac    1380
tatacaagtg tgaagaatgt tctaggatgt tcaaacatgc caggagcctt tcatcccacc    1440
agagaactca cctgaataag aagagtgaat tgctttgtgt cacctgtcag aaaattttca    1500
aacgagtctc tgaccgccga acccatgaga tcatacacat gccagaaaag cctttcaagt    1560
gcagcacatg tgaaaagtcc ttcagccaca agaccaacct gaagtctcat gagatgattc    1620
acacaggaga aatgccttat gtctgttccc tatgtagccg tcgctttcgc caatcatcca    1680
cttaccatcg tcacctgagg aattatcaca gatctgactg aagtatctaa catcctcagc    1740
agagactggt agggcttcag cctcagtatg tcatcttcaa agagagaaga atgttgcaag    1800
taaattgtac tgtcccaata atgatataac atgcttgtgg attgccactt ttatgttttg    1860
ttttgttttg tttttattt tgtgtgtgtg tatgtaattt tttgtctgta tttccatagt    1920
tccacagcat aagttattag aatactttgc tgttaattct tgagttgctt cttgctttta    1980
gacagtgtct ttctggttgg cagctttata cacctgtctt tctggcacta gagttttccaa    2040
acatttctg atctccactt ttattttcta cagtggtcct gacagaggcc tgccattccc    2100
tctgacattt ttctacatgt tggggtttca tcccaagtct tagggttgca agttaaatgc    2160
attgcctctt cagacatctc atgtcatgtc tactgcttac agttcaagaa tatttctcta    2220
```

```
cattactaga acgacgttca aagtggaata ataaataaat aaataatcaa caatt           2275
```

<210> SEQ ID NO 4
<211> LENGTH: 360
<212> TYPE: PRT
<213> ORGANISM: Mus musculus

<400> SEQUENCE: 4

```
Met Ala Ser Gln Gln Ala Pro Ala Lys Asp Leu Gln Thr Asn Asn Leu
 1               5                  10                  15

Glu Phe Thr Pro Thr Asp Ser Ser Gly Val Gln Trp Ala Glu Asp Ile
             20                  25                  30

Ser Asn Ser Pro Ser Ala Gln Leu Asn Phe Ser Pro Ser Asn Asn Gly
         35                  40                  45

Cys Trp Ala Thr Gln Glu Leu Gln Ser Leu Trp Lys Met Phe Asn Ser
     50                  55                  60

Trp Leu Gln Pro Glu Lys Gln Thr Lys Glu Gln Met Ile Ser Gln Leu
 65                  70                  75                  80

Val Leu Glu Gln Phe Leu Leu Thr Gly His Cys Lys Asp Lys Tyr Ala
                 85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Thr
145                 150                 155                 160

Pro Asp Asn Ala Gln Met Pro Val Asp Thr Thr Gln Asp Arg Leu Leu
                165                 170                 175

Ala Thr Gly Gln Glu Asn Ser Glu Asn Glu Cys Asn Thr Ser Cys Asn
            180                 185                 190

Ala Thr Glu Gly Asn Val Gly Glu Ser Cys Ser Gly Asn Glu Met Asp
        195                 200                 205

Ser Ser Leu Ile Ile Gln Lys Glu Gln Tyr Pro Glu His Glu Glu Gly
    210                 215                 220

Asn Val Val Cys Gln Phe Pro Leu Asp Ala Arg Arg Ala Ser Gln Gly
225                 230                 235                 240

Thr Ser Ser His His Val Asp Phe Leu Ser Ala Leu Thr Thr Ala Asp
                245                 250                 255

Val Pro Met Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Lys
        275                 280                 285

Val Tyr Ser Gly Asp Asn Ile Pro Arg Lys Lys Thr Asp Ser Leu Ser
    290                 295                 300

Ile Asn Lys Arg Ile Tyr His Pro Glu Pro Glu Val Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Gly Cys Phe Ser Glu Lys Asp Pro Arg
            340                 345                 350

Glu Val Pro Gly Leu Gln Ser Arg
        355                 360
```

<210> SEQ ID NO 5
<211> LENGTH: 1774
<212> TYPE: DNA
<213> ORGANISM: Mus musculus

<400> SEQUENCE: 5

```
cacagtgcct ccctgggctt cttggcatca cccttgaagt tcactggaga aagaggtgat    60
gtggagaagt aggtaaactt ccctttcttg tggtcttgaa tgtcttttac agtacatccg   120
tcaactgtta gcattttcct aaagtcacaa aacagatact aaactgctat agttgaatct   180
ttcagaccat tgtcaccaca atggcttcac agcaggcacc agcaaaagac cttcagacca   240
acaatttaga gtttactcca actgatagtt ctggtgtgca gtgggcagaa gacatctcta   300
actcaccaag tgctcagcta aacttttccc caagtaacaa tggctgctgg gcaactcagg   360
agctgcaaag tctctggaag atgttcaact cctggttgca gccagaaaag cagactaagg   420
agcagatgat ttctcaattg gtcttggagc agtttctcct cactgggcac tgcaaggaca   480
agtatgcttt gacagagaag tggaaagcca gtggtagcga tatgaggaga ttcatggaga   540
gtctgactga tgagtgcttg aagcctcctg tcatggtcca tgtttcaatg caaggacaag   600
aagccctctt ttctgaaaac atgccattaa agaagtcat caagcttttg aaacaacagc    660
aatctgcaac aaggccaata ccagataatg cacagatgcc agtagacacc acacaagata   720
gattattggc cacaggcaag aaaacagtga aaatgaatgc aacacctctt gcaatgctac   780
tgaagtaaat gttggtgaaa gctgtagtgg aaatgaaaag gactcccttc ttattaccca   840
gaaagaacaa aaccatgagc atgaagaggg gaatgttgtt tgtcaattcc ctcgtggtgc   900
cagaagagca agtcaagaca cctccagtca tcatgtagac ttcccgagtg ctctgactcc   960
tgcagatgtc cccatggagg aacaaccaat ggatttatcc agagaaaaca tctctgagga  1020
caagaacaat tgctataaca cttccaggaa tgcagctact caagtatata gtggtgataa  1080
tattcccagg aacaagacag actcccttt cattaacaag agaatatatc atcctgagcc  1140
tgaggtggga gatattcctt atggagttcc tcaggattct acaagagcaa gtcaaggaac  1200
atctacatgc ctgcaagagt cacttgggga atgtttttct gaaaaagacc caagggaggt  1260
accagggttg cagtctaggc aagagcagcc tatctctgat cctgtccttg gtaagaatca  1320
tgaggcaaac ttaccatgtg aaagtcatca aaagagattc catagagatg ccaaactata  1380
caagtgtgaa gaatgttcta ggatgttcaa acatgccagg agcctttcat cccaccagag  1440
aactcacctg aataagaaga gtgaattgct ttgcatcacc tgtcagaaaa tattcaaacg  1500
agtttctgac cttcgaaccc atgagatcat acacatgtca gaaaagcctt tcaagtgcag  1560
cacatgtgaa aagtccttca gccacaagac caacctgaag tatcatgaga tgattcacac  1620
aggagaaatg ccttatgtct gttccctatg tagccgtcgc tttcgccaat catccactta  1680
ccatcgtcac ctgaggaatt accacagatc tgactgaagt atctaacatc ctcagcagag  1740
actggtaggg cttcagcctc agtatgtcat cttc                              1774
```

<210> SEQ ID NO 6
<211> LENGTH: 195
<212> TYPE: PRT
<213> ORGANISM: Mus musculus

<400> SEQUENCE: 6

```
Met Ala Ser Gln Gln Ala Pro Ala Lys Asp Leu Gln Thr Asn Asn Leu
  1               5                  10                  15
```

```
Glu Phe Thr Pro Thr Asp Ser Ser Gly Val Gln Trp Ala Glu Asp Ile
            20                  25                  30
Ser Asn Ser Pro Ser Ala Gln Leu Asn Phe Ser Pro Ser Asn Asn Gly
        35                  40                  45
Cys Trp Ala Thr Gln Glu Leu Gln Ser Leu Trp Lys Met Phe Asn Ser
    50                  55                  60
Trp Leu Gln Pro Glu Lys Gln Thr Lys Glu Gln Met Ile Ser Gln Leu
65                  70                  75                  80
Val Leu Glu Gln Phe Leu Leu Thr Gly His Cys Lys Asp Lys Tyr Ala
                85                  90                  95
Leu Thr Glu Lys Trp Lys Ala Ser Gly Ser Asp Met Arg Arg Phe Met
            100                 105                 110
Glu Ser Leu Thr Asp Glu Cys Leu Lys Pro Pro Val Met Val His Val
        115                 120                 125
Ser Met Gln Gly Gln Glu Ala Leu Phe Ser Glu Asn Met Pro Leu Lys
    130                 135                 140
Glu Val Ile Lys Leu Leu Lys Gln Gln Ser Ala Thr Arg Pro Ile
145                 150                 155                 160
Pro Asp Asn Ala Gln Met Pro Val Asp Thr Thr Gln Asp Arg Leu Leu
                165                 170                 175
Ala Thr Gly Lys Lys Thr Val Lys Met Asn Ala Thr Pro Leu Ala Met
            180                 185                 190
Leu Leu Lys
    195

<210> SEQ ID NO 7
<211> LENGTH: 2275
<212> TYPE: DNA
<213> ORGANISM: Mus musculus

<400> SEQUENCE: 7
cacagtgcct ccctgggctt cttggcatca cccttgaagt tcaccggaga aagcagtgag     60
gtggaggaat aggtaaactt tccttcctag tggtcttgaa tgtcttttac agtacatcca    120
tcaactgtta gcattttcgt aaagtcacaa aacagatatt aaactactat agttgaatct    180
ttcacaccat tgtcaccaca atggcttcac agcaggcacc agcaaaagac cttcagacca    240
acaatttaga gttactcca actgatagtt ctggtgtgca gtgggcagaa gacatctcta    300
actcaccaag tgctcagcta aacttttccc caagtaacaa tggctgctgg gcaactcagg    360
agctgcaaag tctctggaag atgttcaact cctggttgca gccagaaaag cagactaagg    420
agcagatgat ttctcaactg gtcttggagc agtttctcct cactgggcac tgcaaggaca    480
agtatgcttt gacagagaag tggaaagcca gtggtagcga tatgaggaga ttcatggaga    540
gtctgactga tgagtgcttg aagcctcctg tcatggtcca tgtttcaatg caaggacaag    600
aagccctctt ttctgaaaac atgccattaa agaagtcat caagcttttg aaacaacagc    660
aatctgcaac aaggccaaca ccagataatg agcagatgcc agtagacacc acacaagata    720
gattattggc cacaggacaa gaaaacagtg aaaatgaatg caacaactct tgtaatgcta    780
ctgaagcaaa tgttggtgaa agctgtagtg gaaatgaaat ggactccctt cttattatcc    840
agaaagaaca gcaccctgag catgaagagg ggaatgttgt tgtcaattc cctcatggtg    900 ccagaagagc aagtcaaggc accccagtc atcatgtaga cttccgagt gctccgacta    960 ctgccgatgt ccccatggag gaacaaccaa aggatttatc cagagaaaac atctctgagg   1020
acaagaacaa ttgctataac acttccagaa atgcagctac tcaagtatat agtggtgata   1080
```

| | | | |
|---|---|---|---|
| atattcccag gaacaagtca gactcccttt tcattaacaa gagaatatat catcctgagc | 1140 |
| ctgaggtggg agatattcct tatggagttc ctcaggattc tacaagagca agtcaaggaa | 1200 |
| catctacatg cctgcaagag tcacttgggg aatgttttc tgaaaacgac ccaagggagg | 1260 |
| taccagggtt gcagtctagg caagagcagc ctatctctga tcctgtcctt cttggtaaga | 1320 |
| atcatgaggc aaacttacca tgtgaaagtc atcaaaagag attctgtaga gatgccaaac | 1380 |
| tatacaagtg tgaagaatgt tctaggatgt caaacatgc caggagcctt tcatcccacc | 1440 |
| agagaactca cctgaataag aagagtgaat tgctttgtgt cacctgtcag aaaatgttca | 1500 |
| aacgagtctc tgaccgccga acccatgaga tcatacacat gccagaaaag cctttcaagt | 1560 |
| gcagcacatg tgaaaagtcc ttcagccaca agaccaacct gaagtctcat gagatgattc | 1620 |
| acacaggaga aatgccttat gtctgttccc tatgtagccg tcgctttcgc caatcatcca | 1680 |
| cttaccatcg tcacctgagg aattaccaca gatctgactg aactatctaa catcctcagc | 1740 |
| agagactggt agggcttcag cctcagtatg tcatcttcaa agagagaaga atgttgcaag | 1800 |
| taaattgtac tgtcccaata atgatataac atgcttgtgg attgccactt ttatgttttg | 1860 |
| ttttgttttg ttwtttatkt tgtgtgtgtg tatgtaattt tttgtctgta tttccatatt | 1920 |
| tccacagcat aagttattag aatactttgc tgttaattct tgagttgctt cttgctttta | 1980 |
| gacagtgtct ttctggttgg cagctttata cacctgtctt tctggcacta gagtttccaa | 2040 |
| acatttctg atctccactt ttattttcta cagtgttctt gacagaagcc tggcattccc | 2100 |
| tctgacattt tctacatgtt ggggttttca tcccaagtct tagggttgca agttaaatgc | 2160 |
| attgcctctt cagacatctc atgccatgtc tactgcttac agttcaagaa tatttctcta | 2220 |
| cattactaga acgacgttca aagtggaata ataaataaat aaataatcaa caatt | 2275 |

<210> SEQ ID NO 8
<211> LENGTH: 506
<212> TYPE: PRT
<213> ORGANISM: Mus musculus

<400> SEQUENCE: 8

Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Thr
145                 150                 155                 160

```
Pro Asp Asn Glu Gln Met Pro Val Asp Thr Thr Gln Asp Arg Leu Leu
                165                 170                 175
Ala Thr Gly Gln Glu Asn Ser Glu Asn Glu Cys Asn Asn Ser Cys Asn
            180                 185                 190
Ala Thr Glu Ala Asn Val Gly Glu Ser Cys Ser Gly Asn Glu Met Asp
        195                 200                 205
Ser Leu Leu Ile Ile Gln Lys Glu Gln His Pro Glu His Glu Glu Gly
    210                 215                 220
Asn Val Val Cys Gln Phe Pro His Gly Ala Arg Ala Ser Gln Gly
225                 230                 235                 240
Thr Pro Ser His His Val Asp Phe Pro Ser Ala Pro Thr Thr Ala Asp
                245                 250                 255
Val Pro Met Glu Glu Gln Pro Lys Asp Leu Ser Arg Glu Asn Ile Ser
            260                 265                 270
Glu Asp Lys Asn Asn Cys Tyr Asn Thr Ser Arg Asn Ala Ala Thr Gln
        275                 280                 285
Val Tyr Ser Gly Asp Asn Ile Pro Arg Asn Lys Ser Asp Ser Leu Phe
    290                 295                 300
Ile Asn Lys Arg Ile Tyr His Pro Glu Pro Glu Val Gly Asp Ile Pro
305                 310                 315                 320
Tyr Gly Val Pro Gln Asp Ser Thr Arg Ala Ser Gln Gly Thr Ser Thr
                325                 330                 335
Cys Leu Gln Glu Ser Leu Gly Glu Cys Phe Ser Glu Asn Asp Pro Arg
            340                 345                 350
Glu Val Pro Gly Leu Gln Ser Arg Gln Glu Gln Pro Ile Ser Asp Pro
        355                 360                 365
Val Leu Leu Gly Lys Asn His Glu Ala Asn Leu Pro Cys Glu Ser His
    370                 375                 380
Gln Lys Arg Phe Cys Arg Asp Ala Lys Leu Tyr Lys Cys Glu Glu Cys
385                 390                 395                 400
Ser Arg Met Phe Lys His Ala Arg Ser Leu Ser Ser His Gln Arg Thr
                405                 410                 415
His Leu Asn Lys Lys Ser Glu Leu Leu Cys Val Thr Cys Gln Lys Met
            420                 425                 430
Phe Lys Arg Val Ser Asp Arg Thr His Glu Ile Ile His Met Pro
        435                 440                 445
Glu Lys Pro Phe Lys Cys Ser Thr Cys Glu Lys Ser Phe Ser His Lys
    450                 455                 460
Thr Asn Leu Lys Ser His Glu Met Ile His Thr Gly Glu Met Pro Tyr
465                 470                 475                 480
Val Cys Ser Leu Cys Ser Arg Arg Phe Arg Gln Ser Ser Thr Tyr His
                485                 490                 495
Arg His Leu Arg Asn Tyr His Arg Ser Asp
                500                 505

<210> SEQ ID NO 9
<211> LENGTH: 2268
<212> TYPE: DNA
<213> ORGANISM: Mus musculus

<400> SEQUENCE: 9
cacagtgcct ccctgggctt cttggcatca cccttgaagt tcactggaca aagaggtgag      60
gtggaggagt aggtaaactt cccttcctag tggtcgtgaa tgtctttac agtacatcca     120 tcaactgtta gcattttcat aaagtcacaa aacagatact aaactgctat agttgaatct     180
```

```
ttcacaccat tgtcaccaca atggcttcac agcaggcacc agcaaaagac cttcagacca      240
acaatttaga gtttactcca tctcatagtt ctggtgtgca gtgggtagaa gacatctcta      300
actcaccaag tgctcagcta aacttttctc caagtaacaa tggctgctgg gcaactcagg      360
agctgcaaag tctctggaag atgttcaact cctggttgca gccagaaaag cagactaagg      420
agcagatgat ttctcaactg gtcttggagc agtttctcct cattgggcac tgcaaggaca      480
agtatgcttt gacagagaag tggaaagcca gtggtagcga tatgaggaga ttcatggaga      540
gtctgactga tgagtgcttg aagcctcctg tcatggtcca tgtttcaatg caaggacaag      600
aagctctctt ttctgaaaac atgccattaa aagaagtcat caagcttttg aaacaacagc      660
aatctgcaac aaggccaaca ccagataatg agcagatgcc agtagacacc acacaagata      720
gattattggc cacaggacaa gaaaacagtg aaaatgaatg caacaactct tgtaatgcta      780
ctgaagcaaa tgttggtgaa agctgtagtg gaaatgaaat ggactcoctt cttattatcc      840 agaaagaaca gcaccctgag catgaagagg ggaatgttgt ttttcaattc cctcttgatg      900
ccagaagagc aagtcaaggc aactccagtc atcatgtaga cttccggagt gctccgactc      960
ctgcggatgt ccccatggag gaacaaccaa aggatttatc cagagaaaac atctctgagg     1020
acaagaacaa ttgctataac acttccagga atgcagctac tcaagtatat agaagtgata     1080
atattcccag gaaaaagaca gactcccttt ccattaacaa gagaatatat cattctgagc     1140
ctgaggaggg agatattcct tatggagttc ctcaggattc tacaagagca agtcaaggaa     1200
catctacatg cttgcaagag tcacttgggg aatgttttc tgaaaaagac cctagggagc     1260
taccagggtt ggagtctagg caagaggagc ctatctctga tcctgtcttt cttggtaagg     1320
atcatgaggc aaacttacca tgtgaaagtc atcaaaagag attccgtaga gatgccaaac     1380
tattcaagtg tgaagaatgt tctaggatgt tcaaacatgc caggagcctt tcgtcccacc     1440
agagaactca cctgaataag aagagtgaat tgctttgtgt cacctgtcag aaaatgttca     1500
aacgagtctc tgaccgccga acccatgaga tcatacacat gccagaaaag cctttcaagt     1560
gcagcacatg tgaaaagtcc ttcagccaca agaccaacct gaagtctcat gagatgattc     1620
acacaggaga aatgccttat gtctgttccc tatgtagccg tcgctttcgc caatcatcca     1680
cttaccatcg tcacctgagg aattaccaca gatctgactg aagtatctaa catcctcagc     1740
agagactggt agggcttcag cctcagtatg tcatcttcaa agagagaaga atgttgcaag     1800
taaattgtac tgtcccaata atgatataac atgcttgtgg attgccactt ttatgttttg     1860
ttttttattg tgtgtgtgtg tgtatgtaat tttttgtctg taatttccat agttccacag     1920
cataagttat tagaatactt tgctgttaat tcttgagttg cttcttgctt ttagacagtg     1980
tctttctggt tggcagcttt atacacctgt ctttctggca ctagagtttc caaacatttt     2040
ctgatctcca ctttattct ctacagtggt cctgacagag gcctgccatt ccctctgaca     2100
ttttttaaca tgtggggtt tcatcccaag tcttagggtt gcaagttaaa tgcattgcct     2160
cttcagacat ctcatgtcat gtctactgct tacagttcaa gaatatttct ctacattact     2220
agaatgacgt tcaaagtgga ataataaata aaaaaataat caacaatt                  2268
```

<210> SEQ ID NO 10
<211> LENGTH: 506
<212> TYPE: PRT
<213> ORGANISM: Mus musculus

<400> SEQUENCE: 10

```
Met Ala Ser Gln Gln Ala Pro Ala Lys Asp Leu Gln Thr Asn Asn Leu
 1               5                  10                  15

Glu Phe Thr Pro Ser His Ser Ser Gly Val Gln Trp Val Glu Asp Ile
                20                  25                  30

Ser Asn Ser Pro Ser Ala Gln Leu Asn Phe Ser Pro Ser Asn Asn Gly
            35                  40                  45

Cys Trp Ala Thr Gln Glu Leu Gln Ser Leu Trp Lys Met Phe Asn Ser
 50                  55                  60

Trp Leu Gln Pro Glu Lys Gln Thr Lys Glu Gln Met Ile Ser Gln Leu
 65                  70                  75                  80

Val Leu Glu Gln Phe Leu Leu Ile Gly His Cys Lys Asp Lys Tyr Ala
                 85                  90                  95

Leu Thr Glu Lys Trp Lys Ala Ser Gly Ser Asp Met Arg Arg Phe Met
                100                 105                 110

Glu Ser Leu Thr Asp Glu Cys Leu Lys Pro Pro Val Met Val His Val
            115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Ser Ala Thr Arg Pro Thr
145                 150                 155                 160

Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
                180                 185                 190

Ala Thr Glu Ala Asn Val Gly Val Ser Cys Ser Gly Asn Glu Met Asp
    195                 200                 205

Ser Leu Leu Ile Ile Gln Lys Glu Gln His Pro Glu His Glu Glu Gly
    210                 215                 220

Asn Val Val Phe Gln Phe Pro Leu Asp Ala Arg Arg Ala Ser Gln Gly
225                 230                 235                 240

Asn Ser Ser His His Val Asp Phe Arg Ser Ala Pro Thr Pro Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
            275                 280                 285

Val Tyr Arg Ser Asp Asn Ile Pro Arg Lys Lys Thr Asp Ser Leu Ser
    290                 295                 300

Ile Asn Lys Arg Ile Tyr His Ser Glu Pro Glu Glu Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Glu Cys Phe Ser Glu Lys Asp Pro Arg
                340                 345                 350

Glu Leu Pro Gly Leu Glu Ser Arg Gln Glu Pro Ile Ser Asp Pro
                355                 360                 365

Val Phe Leu Gly Lys Asp His Glu Ala Asn Leu Pro Cys Glu Ser His
    370                 375                 380

Gln Lys Arg Phe Arg Arg Asp Ala Lys Leu Phe Lys Cys Glu Glu Cys
385                 390                 395                 400

Ser Arg Met Phe Lys His Ala Arg Ser Leu Ser Ser His Gln Arg Thr
                405                 410                 415

His Leu Asn Lys Lys Ser Glu Leu Leu Cys Val Thr Cys Gln Lys Met
```

```
                420               425               430
Phe Lys Arg Val Ser Asp Arg Arg Thr His Glu Ile Ile His Met Pro
            435               440               445

Glu Lys Pro Phe Lys Cys Ser Thr Cys Glu Lys Ser Phe Ser His Lys
        450               455               460

Thr Asn Leu Lys Ser His Glu Met Ile His Thr Gly Glu Met Pro Tyr
465               470               475               480

Val Cys Ser Leu Cys Ser Arg Arg Phe Arg Gln Ser Ser Thr Tyr His
                485               490               495

Arg His Leu Arg Asn Tyr His Arg Ser Asp
            500               505

<210> SEQ ID NO 11
<211> LENGTH: 1774
<212> TYPE: DNA
<213> ORGANISM: Mus musculus

<400> SEQUENCE: 11
```

| | | | | | |
|---|---|---|---|---|---|
| cacagtgcct | ccctgggctt | cttggcatca | ccattgaagt | tcactggaga | aagaggtgag | 60 |
| gtggagaagt | aggtaaactt | ccctttcttg | tggtcttgaa | tgtcttttac | agtacatccg | 120 |
| tcaactgtta | gcattttcct | aaagtcacaa | acagatact | aaactgctat | agttgaatct | 180 |
| ttcagaccat | tgtcaccaca | atggcttcac | agcaggcacc | agcaaaagac | cttcagacca | 240 |
| acaatttaga | gtttactcca | actgatagtt | ctggtgtgca | gtgggcagaa | gacatctcta | 300 |
| actcaccaag | tgctcagcta | aacttttccc | caagtaacaa | tggctgctgg | gcaactcagg | 360 |
| agctgcaaag | tctctggaag | atgttcaact | cctggttgca | gccagaaaag | cagactaagg | 420 |
| agcagatgat | ttctcaactg | gtcttggagc | agtttctcct | cactgggcac | tgcaaggaca | 480 |
| agtatgcttt | gacagagaag | tggaaagcca | gtggtagcga | tatgaggaga | ttcatggaga | 540 |
| gtctgactga | tgagtgcttg | aagcctcctg | tcatggtcca | tgtttcaatg | caaggacaag | 600 |
| aagccctctt | ttctgaaaac | atgccattaa | agaagtcat | caagcttttg | aaacaacagc | 660 |
| aatctgcaac | aaggccaata | ccagataatg | agcagatgcc | agtagacacc | acacaagata | 720 |
| gattattggc | cacaggcaag | aaaacagtga | aaatgaatgc | aacacctctt | gcaatgctac | 780 |
| tgaagtaaat | gttggtgaaa | gctgtagtgg | aaatgaaaag | gactcccttc | ttattaccca | 840 |
| gaaagaacaa | aaccatgagc | atgaagaggg | gaatgttgtt | tgtcaattcc | ctcgtggtgc | 900 |
| cagaagagca | agtcaagaca | cctccagtca | tcatgtagac | ttcccgagtg | ctctgactcc | 960 |
| tgcagatgtc | cccatggagg | aacaaccaat | ggatttatcc | agagaaaaca | tctctgagga | 1020 |
| caagaacaat | tgctataaca | cttccaggaa | tgcagctact | caagtatata | atggtgataa | 1080 |
| tattcccagg | aacaagacag | actccctttt | cattaacaag | agaatatatc | atcctgagcc | 1140 |
| tgaggtggga | gatattcctt | atggagttcc | tcaggattct | acaagagcaa | gtcaaggaac | 1200 |
| atctacatgc | ctgcaagagt | cacttgggga | atgttttttct | gaaaaagacc | caagggaggt | 1260 |
| accagggttg | cagtctaggc | aagagcagcc | tatctctgat | cctgtccttg | gtaagaatca | 1320 |
| tgaggcaaac | ttaccatgtg | aaagtcatca | aaagagattc | catagagatg | ccaaactata | 1380 |
| caagtgtgaa | gaatgttcta | ggatgttcaa | acatgccagg | agcctttcat | cccaccagag | 1440 |
| aactcacctg | aataagaaga | gtgaattgct | ttgcatcacc | tgtcagaaaa | tattcaaacg | 1500 |
| agtttctgac | cttcgaaccc | atgagatcat | acacatgtca | gaaaagcctt | tcaagtgcag | 1560 |
| cacatgtgaa | aagtccttca | gccacaagac | caacctgaag | tatcatgaga | tgattcacac | 1620 |

```
aggagaaatg ccttatgtct gttccctatg tagccgtcgc tttcgccaat catccactta    1680
ccatcgtcac ctgaggaatt accacagatc tgactgaagt atctaacatc ctcagcagag    1740
actggtaggg cttcagcctc agtatgtcat cttc                                1774
```

<210> SEQ ID NO 12
<211> LENGTH: 195
<212> TYPE: PRT
<213> ORGANISM: Mus musculus

<400> SEQUENCE: 12

```
Met Ala Ser Gln Gln Ala Pro Ala Lys Asp Leu Gln Thr Asn Asn Leu
 1               5                  10                  15

Glu Phe Thr Pro Thr Asp Ser Ser Gly Val Gln Trp Ala Glu Asp Ile
             20                  25                  30

Ser Asn Ser Pro Ser Ala Gln Leu Asn Phe Ser Pro Ser Asn Asn Gly
         35                  40                  45

Cys Trp Ala Thr Gln Glu Leu Gln Ser Leu Trp Lys Met Phe Asn Ser
     50                  55                  60

Trp Leu Gln Pro Glu Lys Gln Thr Lys Glu Gln Met Ile Ser Gln Leu
 65                  70                  75                  80

Val Leu Glu Gln Phe Leu Leu Thr Gly His Cys Lys Asp Lys Tyr Ala
                 85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Ser Ala Thr Arg Pro Ile
145                 150                 155                 160

Pro Asp Asn Glu Gln Met Pro Val Asp Thr Thr Gln Asp Arg Leu Leu
                165                 170                 175

Ala Thr Gly Lys Lys Thr Val Lys Met Asn Ala Thr Pro Leu Ala Met
            180                 185                 190

Leu Leu Lys
        195
```

<210> SEQ ID NO 13
<211> LENGTH: 2273
<212> TYPE: DNA
<213> ORGANISM: Mus musculus

<400> SEQUENCE: 13

```
cacagtgcct ccctgggctt cttggcatca cccttgaagt tcactggaga aagaggtgag      60
gtggaggaat aggtaaactt tccttcctag tggtcttgaa tgtcttttac agtacatcca     120
tcaactgtta gcattttcgt aaagtcacaa aacagatatt aaactactat agttgaatct     180
ttcacaccat tgtcaccaca atggcttcac agcaggcacc agcaaaagac cttcagacca     240
acaatttaga gtttactcca actgatagtt ctggtgtgca gtgggcagaa gacatctcta     300
actcaccaag tgctcagcta aacttttccc caagtaacaa tggctgctgg gcaactcagg     360
agctgcaaag tctctggaag atgttcaact cctggttgca gccagaaaag cagactaagg     420
agcagatgat tctcaactg tcttggagc agtttctcct cactgggcac tgcaaggaca     480
agtatgcttt gactgagaag tggaaagcca gtggtagcga tatgaggaga ttcatggaga     540
```

```
gtctgactga tgagtgcttg aagcctcctg tcatggtcca tgtttcaatg caaggacaag    600
aagccctctt ttctgaaaac atgccattaa agaagtcat  caagcttttg aaacaacagc    660
aatctgcaac aaggccaaca ccagataatg agcagatgcc agtagacacc acacaagata    720
gattattggc cacaggacaa gaaaacagtg aaaatgaatg caacaactct tgtaatgcta    780
ctgaagcaaa tgttggtgaa agctgtagtg gaaatgaaat ggactcccct cttattatgc    840
agaaagaaca gcaccctgag catgaagagg ggaatgttgt tgtcaattc  cctcatggtg    900
ccagaagagc aagtcaaggc accccagtc  atcatgtaga cttcccgagt gctccgacta    960
ctgccgatgt ccccatggag gaacaaccaa aggatttatc cagagaaaac atctctgagg   1020
acaagaacaa ttgctataac acttccagaa atgcagctac tcaagtatat agtggtgata   1080
atattcccag gaacaagtca gactcccttt tcattaacaa gagaatatat catcctgagc   1140
ctgaggtggg agatattcct tatggagttc ctcaggattc tacaagagca agtcaaggaa   1200
catctacatg cctgcaagag tcacttgggg aatgtttttc tgaaaagac  cctagggagg   1260
taccagggtt gcagtctagg caagagcagc ttatctctga tcctgtcctt cttggtaaga   1320
atcatgaggc aaacttacca tgtgaaagtc atcaaaagag attctgtaga gatgccaaac   1380
tatacaagtg tgaagaatgt tctaggatgt tcaaacatgc caggagcctt tcatcccacc   1440
agagaactca cctgaataag aagagtgaat tgctttgtgt cacctgtcag aaaatgttca   1500
aacgagtctc tgaccgccga acccatgaga tcatacacat gccagaaaag cctttcaagt   1560
gcagcacatg tgaaaagtcc ttcagccaca agaccaacct gaagtctcat gagatgattc   1620
acacaggaga aatgccttat gtctgttccc tatgtagccg tcgctttcgc caatcatcca   1680
cttaccatcg tcacctgagg aattaccaca gatctgactg aactatctaa catcctcagc   1740
agagactggt agggcttcag cctcagtatg tcatcttcaa agagagaaga atgttgcaag   1800
taaattgtac tgtcccaata atgatataac atgcttgtgg attgccactt ttatgttttg   1860
ttttgttttt tattttgtgt gtgtgtgtat gtaattttt  gtctgtattt ccatagttcc   1920
acagcataag ttattagaat actttgctgt taattcttga gttgcttctt gcttttagac   1980
agtgtctttc tggttgacag ctttataaac ctgtctttct ggcactagag tttccaaaca   2040
ttttctgatc tccacttttta ttctctacag tgttcttgac agaagcctgg cattccctct   2100
gacattttc tacatgttgg ggttttcatc ccaagtctta gggttgcaag ttaaatgcat    2160
tgcctcttca gacatctcat gccctgtcta ctgcttacag ttcaagaata tttctctaca   2220
ttactagaac gacattcaaa gtggaataat aaataaataa ataatcaaca att           2273
```

<210> SEQ ID NO 14
<211> LENGTH: 506
<212> TYPE: PRT
<213> ORGANISM: Mus musculus

<400> SEQUENCE: 14

```
Met Ala Ser Gln Gln Ala Pro Ala Lys Asp Leu Gln Thr Asn Asn Leu
 1               5                  10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
```

```
            65                  70                  75                  80
Val Leu Glu Gln Phe Leu Leu Thr Gly His Cys Lys Asp Lys Tyr Ala
                    85                  90                  95
Leu Thr Glu Lys Trp Lys Ala Ser Gly Ser Asp Met Arg Arg Phe Met
                   100                 105                 110
Glu Ser Leu Thr Asp Glu Cys Leu Lys Pro Val Met Val His Val
                   115                 120                 125
Ser Met Gln Gly Gln Glu Ala Leu Phe Ser Glu Asn Met Pro Leu Lys
    130                 135                 140
Glu Val Ile Lys Leu Leu Lys Gln Gln Ser Ala Thr Arg Pro Thr
145                 150                 155                 160
Pro Asp Asn Glu Gln Met Pro Val Asp Thr Thr Gln Asp Arg Leu Leu
                   165                 170                 175
Ala Thr Gly Gln Glu Asn Ser Glu Asn Glu Cys Asn Asn Ser Cys Asn
                   180                 185                 190
Ala Thr Glu Ala Asn Val Gly Glu Ser Cys Ser Gly Asn Glu Met Asp
                   195                 200                 205
Ser Leu Leu Ile Met Gln Lys Glu Gln His Pro Glu His Glu Glu Gly
    210                 215                 220
Asn Val Val Cys Gln Phe Pro His Gly Ala Arg Ala Ser Gln Gly
225                 230                 235                 240
Thr Pro Ser His His Val Asp Phe Pro Ser Ala Pro Thr Thr Ala Asp
                   245                 250                 255
Val Pro Met Glu Glu Gln Pro Lys Asp Leu Ser Arg Glu Asn Ile Ser
                   260                 265                 270
Glu Asp Lys Asn Asn Cys Tyr Asn Thr Ser Arg Asn Ala Ala Thr Gln
                   275                 280                 285
Val Tyr Ser Gly Asp Asn Ile Pro Arg Asn Lys Ser Asp Ser Leu Phe
                   290                 295                 300
Ile Asn Lys Arg Ile Tyr His Pro Glu Pro Glu Val Gly Asp Ile Pro
305                 310                 315                 320
Tyr Gly Val Pro Gln Asp Ser Thr Arg Ala Ser Gln Gly Thr Ser Thr
                   325                 330                 335
Cys Leu Gln Glu Ser Leu Gly Glu Cys Phe Ser Glu Lys Asp Pro Arg
                   340                 345                 350
Glu Val Pro Gly Leu Gln Ser Arg Gln Glu Gln Leu Ile Ser Asp Pro
                   355                 360                 365
Val Leu Leu Gly Lys Asn His Glu Ala Asn Leu Pro Cys Glu Ser His
    370                 375                 380
Gln Lys Arg Phe Cys Arg Asp Ala Lys Leu Tyr Lys Cys Glu Glu Cys
385                 390                 395                 400
Ser Arg Met Phe Lys His Ala Arg Ser Leu Ser Ser His Gln Arg Thr
                   405                 410                 415
His Leu Asn Lys Lys Ser Glu Leu Leu Cys Val Thr Cys Gln Lys Met
                   420                 425                 430
Phe Lys Arg Val Ser Asp Arg Thr His Glu Ile Ile His Met Pro
                   435                 440                 445
Glu Lys Pro Phe Lys Cys Ser Thr Cys Glu Lys Ser Phe Ser His Lys
    450                 455                 460
Thr Asn Leu Lys Ser His Glu Met Ile His Thr Gly Glu Met Pro Tyr
465                 470                 475                 480
Val Cys Ser Leu Cys Ser Arg Arg Phe Arg Gln Ser Ser Thr Tyr His
                   485                 490                 495
```

Arg His Leu Arg Asn Tyr His Arg Ser Asp
            500                 505

<210> SEQ ID NO 15
<211> LENGTH: 9396
<212> TYPE: DNA
<213> ORGANISM: Artificial Sequence
<220> FEATURE:
<223> OTHER INFORMATION: Synthetic polynucleotide

<400> SEQUENCE: 15

| | | | | | |
|---|---|---|---|---|---|
| cgcatagtta | agccagtatc | tgctccctgc | ttgtgtgttg | gaggtcgctg | agtagtgcgc | 60 |
| gagcaaaatt | taagctacaa | caaggcaagg | cttgaccgac | aattgcatga | agaatctgct | 120 |
| tagggttagg | cgttttgcgc | tgcttcgcga | tgtacgggcc | agatatacgc | gttgacattg | 180 |
| attattgact | agttattaat | agtaatcaat | tacggggtca | ttagttcata | gcccatatat | 240 |
| ggagttccgc | gttacataac | ttacggtaaa | tggcccgcct | ggctgaccgc | ccaacgaccc | 300 |
| ccgcccattg | acgtcaataa | tgacgtatgt | tcccatagta | acgccaatag | ggactttcca | 360 |
| ttgacgtcaa | tgggtggagt | atttacggta | aactgcccac | ttggcagtac | atcaagtgta | 420 |
| tcatatgcca | agtacgcccc | ctattgacgt | caatgacggt | aaatggcccg | cctggcatta | 480 |
| tgcccagtac | atgaccttat | gggactttcc | tacttggcag | tacatctacg | tattagtcat | 540 |
| cgctattacc | atggtgatgc | ggttttggca | gtacatcaat | gggcgtggat | agcggtttga | 600 |
| ctcacgggga | tttccaagtc | tccaccccat | tgacgtcaat | gggagtttgt | tttggcacca | 660 |
| aaatcaacgg | gactttccaa | aatgtcgtaa | caactccgcc | ccattgacgc | aaatgggcgg | 720 |
| taggcgtgta | cggtgggagg | tctatataag | cagagctctc | tggctaacta | gagaacccac | 780 |
| tgcttactgg | cttatcgaaa | ttaatacgac | tcactatagg | gagacccaag | ctggctagtt | 840 |
| aagctgagca | tcaacaagtt | tgtacaaaaa | agcaggctcc | gaattcgccc | ttgacgcgcg | 900 |
| acgcgtgtcc | tgctattctg | tgcattgaaa | catgtcatgt | ctgtgtccct | gatgttttac | 960 |
| ttgaagaata | tggcatacaa | gttccttctt | ctttgcttta | tagaatatat | tttaaattat | 1020 |
| aataatttcc | tctctaaaat | aatgttttg | ttaagaccta | ttaatttgtt | ataaattttg | 1080 |
| ttgggattac | aaatactttt | ctgagaaaag | tttgcatgtt | gtacaaactc | tattcatata | 1140 |
| aaatacctttt | tcatacaaaa | gaagaattgc | tgttttatcc | ccattctaac | tcttagtata | 1200 |
| aataaaataa | tgcagtgggt | tgttctgatg | ctgcttatat | tatcatgcta | aatattggct | 1260 |
| tcttaatctg | tggtcgtcca | caaagtacag | agccacacat | ccaccaaatg | atgttatttg | 1320 |
| aatattgtcc | cgaaatacaa | ctggttaaaa | aaaaaaaaaa | aaaaaaagc | aacttgctat | 1380 |
| gactggtcat | ctaagggaga | aaggtggaat | ttgaggatta | agtgaagaga | ttgctggtag | 1440 |
| aggaagagaa | agaagaaaga | agacttaagc | ggagatggtt | gccatgggaa | gagatgaaat | 1500 |
| ataaattctt | ggaacagaga | aatagcaagt | ataaggact | tgatcgttgg | ggaataagct | 1560 |
| gaaatagctg | taaatctgcc | ttatttaggc | ttgagtttgt | aaataaaata | gctagattgt | 1620 |
| gttttttttt | atatggacaa | gctagcatta | tggatcccttt | ccaacagcaa | caaccaataa | 1680 |
| atgatttaaa | agcatggctt | ctaccttcct | agtagtagcg | gttccaggac | aaccttactt | 1740 |
| ctatcatctt | tttcttcttc | ttcttcttga | tgcttttgtg | cttttttttt | tttttttttt | 1800 |
| tttttttttt | tttttttttt | ttttggtgac | accttctgtt | catgcaagcc | tggctatgtt | 1860 |
| tgagctctat | ttgaaatcca | gacttgcctc | aaagtgatag | agatgcttct | gcatctgttt | 1920 |
| tctgatctag | gattaagtgt | gtagcaggga | ttaaaggcac | taacctcctt | caagtaatct | 1980 |

```
aattgctaaa ttgaattgtg cccttgaaat tcactttcag gaagaaaata gtgaacaaca    2040
gtaaagtgtt tattgttctc atgaaaaaac actttcatct gaatgtttct tcttgttagt    2100
attgcattaa ttcattaata tactgaacat catcaatagc aaaaaaaaaa caaatgatac    2160
atttttacat ggtgagtcaa tcattgttgt aacaaatggc taattcattt gaagaatttg    2220
tagtgctttc tttgtcatgt ggcatttttt tttccataaa gggaagggca gctttaggtt    2280
taagcattca aaatttatgg ttttgtgaat gtaaaaaatt ttagaagttg taaatcactg    2340
attttccatc ctatttgggg taagggaaaa taaggttcta tgttttggac tgaagtttag    2400
cacaatctca gtgtttgaag ataaaacatc aacatgtgaa tttaggggtc acaattgaac    2460
ctatcaatta gcatgattgg acaaagcaat tcacaaaggc aaccacgttt aaatccacca    2520
ctctggaatt aatggcaagg atgtgtcaac ctgatccaca ctgtagggct attatgtcta    2580
ggcatacaag ggaaaaaaat tgtctctaga tgaagtaaaa gaaacagag acagaaaaac     2640 aaaaaggatg tgtgaagtag tgaggtcact ctgggatgtc agcactgagg agttaaaagt    2700
tatatgattg tagtgcaaga tcattctgaa caagttagtg agattgtgag cagactagga    2760
taccatatag acacttgtaa aaaacaaac aaaacaaaaa acaaatgaac aaaccaaaca     2820
tgagagagag atggaaagat agagaaaaca agagagaaca acaaagacca ccacattttg    2880
ccacaaattt taatctctcc ctagaataca gtcctcatat gatgtccatg ttttcgcaat    2940
aggcaatgca cattcctctc taccaaaaga tacaagttcc cttcagcctc catctttact    3000
atattgtgct acagacacct tatggattct tcctgcccta tctgatccca ctatcaagga    3060
ttctacagag ttcactgaag cacttagggt ccaatctctc tagaaaccag gaaattttaa    3120
caagttttca ttgactacta tgtgagaaca caggatcaga ggtcatagaa gataaatgcc    3180
aatcttggaa ttcctcttca gtgtggtact atttccattc actacagtga cttacaacac    3240
ttgactagga gatgatcttc ttccaaagaa gagtcaatca ttgcattaga gatgcaaaac    3300
tagagctgag ttaggattcc ttatgtgatt caatcagcag gaaaaaatgt ctttccttat    3360
tttgtttgct tgcttgtatt tgattccccc ttttggcatt atctgttcct ctgggtcaga    3420
ctgaccttgg atctctgggc ttaataggca gtgctgggga ctactgactc tcctgattca    3480
atttctatta ctttgagtac tatggataaa atggtaatct gccccaccca ggaacaggag    3540
ttttgataga atcactgtgt gaatttaatc gtcatcagta actgactaac ggaagccagg    3600
cgctataaaa gggaaccaat cctaatagaa cctcagatga agcagagcca aggcagagac    3660
acacagtgcc tccctgggct tcttggcatc accttgaag ttcaccggag aaagcagtga     3720
ggtggaggaa taggtaaact ttccttccta gtggtcttga atgtgtaagt atatgtgtat    3780
ttatgtgtgt gtatgtgtgt ttatttgtgg acttgtgaga agattcatca caattatggg    3840
gagatctcag tagttcaata ttgccttttg gaagctttcc tgatcaagag gttgattttt    3900
ctaaactcta aagaaaactc tgagttggta atcattcagg tatgtgcgtg gatatttgtt    3960
tgcctctctg tgaatttaat attcctgatt attcatttta aatattttct tatgaaagta    4020
ttattctctg gtgctttaga atgagacaga agggtgaaac ttaaaatttg aggaacagca    4080
gaataactcc catcttttcc aaagggggaa cagacaacat tgctgtgttc ttaagatctc    4140
atgacagatc taagcaccct agatacagga cttttctggtt attgagtcaa ttttttttct   4200
acttttcagt tgttttgccc atttccaatt ccatgcaagc agattgaaag gactatagtg    4260
aaacatttac tgtcaggaac ccataaaacc atctgtgaca caaatctcat ttggttttgt    4320
```

```
gtttgttttg ttaacattaa ttatgtgttt cttccttttt taaattcaca gcttttacag    4380
tacatccatc aactgttagc attttcgtaa agtcacaaaa cagatattaa actactatag    4440
ttgaatcttt cacaccattg tcaccacagt taacaagggc gaattcgacc cagctttctt    4500
gtacaaagtg gttgatgctg ttaacatggt gagcaagggc gaggagctgt tcaccggggt    4560
ggtgcccatc ctggtcgagc tggacggcga cgtaaacggc cacaagttca gcgtgtccgg    4620
cgagggcgag ggcgatgcca cctacggcaa gctgaccctg aagttcatct gcaccaccgg    4680
caagctgccc gtgccctggc ccaccctcgt gaccaccttc acctacggcg tgcagtgctt    4740
cgcccgctac cccgaccaca tgaagcagca cgacttcttc aagtccgcca tgcccgaagg    4800
ctacgtccag gagcgcacca tcttcttcaa ggacgacggc aactacaaga cccgcgccga    4860
ggtgaagttc gagggcgaca ccctggtgaa ccgcatcgag ctgaagggca tcgacttcaa    4920
ggaggacggc aacatcctgg ggcacaagct ggagtacaac tacaacagcc acaaggtcta    4980
tatcaccgcc gacaagcaga agaacggcat caaggtgaac ttcaagaccc gccacaacat    5040
cgaggacggc agcgtgcagc tcgccgacca ctaccagcag aacaccccca tcggcgacgg    5100
ccccgtgctg ctgcccgaca accactacct gagcacccag tccgccctga gcaaagaccc    5160
caacgagaag cgcgatcaca tggtcctgct ggagttcgtg accgccgccg ggatcactct    5220
cggcatggac gagctgtaca gtaatgata agtttaaacg ggggaggcta actgaaacac    5280
ggaaggagac aataccggaa ggaacccgcg ctatgacgga aataaaaaga cagaataaaa    5340
cgcacgggtg ttgggtcgtt tgttcataaa cgcggggttc ggtcccaggg ctggcactct    5400
gtcgataccc caccgagacc ccattggggc caatacgccc gcgtttcttc cttttcccca    5460
ccccaccccc caagttcggg tgaaggccca gggctcgcag ccaacgtcgg gcggcaggc    5520 cctgccatag cagatctgcg cagctgggc tctagggggt atccccacgc gccctgtagc    5580
ggcgcattaa gcgcggcggg tgtggtggtt acgcgcagcg tgaccgctac acttgccagc    5640
gccctagcgc ccgctccttt cgctttcttc ccttcctttc tcgccacgtt cgccggcttt    5700
ccccgtcaag ctctaaatcg ggggctccct ttagggttcc gatttagtgc tttacggcac    5760
ctcgacccca aaaaacttga ttagggtgat ggttcacgta gtgggccatc gccctgatag    5820 acggttttc gccctttgac gttggagtcc acgttcttta atagtggact cttgttccaa    5880
actggaacaa cactcaaccc tatctcggtc tattcttttg atttataagg gattttgccg    5940
atttcggcct attggttaaa aaatgagctg atttaacaaa aatttaacgc gaattaattc    6000
tgtggaatgt gtgtcagtta gggtgtggaa agtccccagg ctccccagca ggcagaagta    6060
tgcaaagcat gcatctcaat tagtcagcaa ccaggtgtgg aaagtcccca ggctccccag    6120
caggcagaag tatgcaaagc atgcatctca attagtcagc aaccatagtc cgcccctaa    6180 ctccgcccat cccgccccta actccgccca gttccgccca ttctccgccc catggctgac    6240 taatttttt tatttatgca gaggccgagg ccgcctctgc ctctgagcta ttccagaagt    6300
agtgaggagg ctttttgga ggcctaggct tttgcaaaaa gctcccggga gcttgtatat    6360
ccattttcgg atctgatcag cacgtgttga caattaatca tcggcatagt atatcggcat    6420
agtataatac gacaaggtga ggaactaaac catggccaag cctttgtctc aagaagaatc    6480 cacctcatt gaaagagcaa cggctacaat caacagcatc cccatctctg aagactacag    6540
cgtcgccagc gcagctctct ctagcgacgg ccgcatcttc actggtgtca atgtatatca    6600
ttttactggg ggaccttgtg cagaactcgt ggtgctgggc actgctgctg ctgcggcagc    6660
tggcaacctg acttgtatcg tcgcgatcgg aaatgagaac aggggcatct tgagcccctg    6720
```

```
cggacggtgc cgacaggtgc ttctcgatct gcatcctggg atcaaagcca tagtgaagga    6780
cagtgatgga cagccgacgg cagttgggat tcgtgaattg ctgccctctg gttatgtgtg    6840
ggagggctaa gcacttcgtg gccgaggagc aggactgaca cgtgctacga gatttcgatt    6900
ccaccgccgc cttctatgaa aggttgggct tcggaatcgt tttccgggac gccggctgga    6960
tgatcctcca gcgcggggat ctcatgctgg agttcttcgc ccaccccaac ttgtttattg    7020
cagcttataa tggttacaaa taaagcaata gcatcacaaa tttcacaaat aaagcatttt    7080
tttcactgca ttctagttgt ggtttgtcca aactcatcaa tgtatcttat catgtctgta    7140
taccgtcgac ctctagctag agcttggcgt aatcatggtc atagctgttt cctgtgtgaa    7200
attgttatcc gctcacaatt ccacacaaca tacgagccgg aagcataaag tgtaaagcct    7260
ggggtgccta atgagtgagc taactcacat taattgcgtt gcgctcactg cccgctttcc    7320
agtcgggaaa cctgtcgtgc cagctgcatt aatgaatcgg ccaacgcgcg gggagaggcg    7380
gtttgcgtat tgggcgctct tccgcttcct cgctcactga ctcgctgcgc tcggtcgttc    7440
ggctgcggcg agcggtatca gctcactcaa aggcggtaat acggttatcc acagaatcag    7500
gggataacgc aggaaagaac atgtgagcaa aaggccagca aaaggccagg aaccgtaaaa    7560
aggccgcgtt gctggcgttt ttccataggc tccgcccccc tgacgagcat cacaaaaatc    7620
gacgctcaag tcagaggtgg cgaaacccga caggactata agataccag gcgtttcccc    7680 ctggaagctc cctcgtgcgc tctcctgttc cgaccctgcc gcttaccgga tacctgtccg    7740
cctttctccc ttcgggaagc gtggcgcttt ctcatagctc acgctgtagg tatctcagtt    7800
cggtgtaggt cgttcgctcc aagctgggct gtgtgcacga accccccgtt cagcccgacc    7860
gctgcgcctt atccggtaac tatcgtcttg agtccaaccc ggtaagacac gacttatcgc    7920
cactggcagc agccactggt aacaggatta gcagagcgag gtatgtaggc ggtgctacag    7980
agttcttgaa gtggtggcct aactacggct acactagaag aacagtattt ggtatctgcg    8040
ctctgctgaa gccagttacc ttcggaaaaa gagttggtag ctcttgatcc ggcaaacaaa    8100
ccaccgctgg tagcggtggt ttttttgttt gcaagcagca gattacgcgc agaaaaaaag    8160
gatctcaaga agatcctttg atcttttcta cggggtctga cgctcagtgg aacgaaaact    8220
cacgttaagg gattttggtc atgagattat caaaaaggat cttcacctag atccttttaa    8280
attaaaaatg aagttttaaa tcaatctaaa gtatatatga gtaaacttgg tctgacagtt    8340
accaatgctt aatcagtgag gcacctatct cagcgatctg tctatttcgt tcatccatag    8400
ttgcctgact ccccgtcgtg tagataacta cgatacggga gggcttacca tctggcccca    8460
gtgctgcaat gataccgcga gacccacgct caccggctcc agatttatca gcaataaacc    8520
agccagccgg aagggccgag cgcagaagtg gtcctgcaac tttatccgcc tccatccagt    8580
ctattaattg ttgccgggaa gctagagtaa gtagttcgcc agttaatagt ttgcgcaacg    8640
ttgttgccat tgctacaggc atcgtggtgt cacgctcgtc gtttggtatg gcttcattca    8700
gctccggttc ccaacgatca aggcgagtta catgatcccc catgttgtgc aaaaaagcgg    8760
ttagctcctt cggtcctccg atcgttgtca gaagtaagtt ggccgcagtg ttatcactca    8820
tggttatggc agcactgcat aattctctta ctgtcatgcc atccgtaaga tgcttttctg    8880
tgactggtga gtactcaacc aagtcattct gagaatagtg tatgcggcga ccgagttgct    8940
cttgcccggc gtcaatacgg gataataccg cgccacatag cagaacttta aaagtgctca    9000
tcattggaaa acgttcttcg gggcgaaaac tctcaaggat cttaccgctg ttgagatcca    9060
```

```
                                                            -continued gttcgatgta  acccactcgt  gcacccaact  gatcttcagc  atctttact   ttcaccagcg   9120 tttctgggtg  agcaaaaaca  ggaaggcaaa  atgccgcaaa  aaagggaata  agggcgacac   9180
ggaaatgttg  aatactcata  ctcttccttt  ttcaatatta  ttgaagcatt  tatcagggtt   9240
attgtctcat  gagcggatac  atatttgaat  gtatttagaa  aaataaacaa  atagggttc    9300 cgcgcacatt  tccccgaaaa  gtgccacctg  acgtcgacgg  atcgggagat  ctcccgatcc   9360
cctatggtgc  actctcagta  caatctgctc  tgatgc                               9396
```

ZSCAN4 AS A MARKER FOR PANCREATIC STEM CELLS AND PROGENITOR CELLS AND USE THEREOF

CROSS REFERENCE TO RELATED APPLICATIONS

This application is a U.S. National Phase application of PCT/US2012/022575, filed Jan. 25, 2012, which claims priority to U.S. Provisional Application Ser. No. 61/436,068 filed Jan. 25, 2011, the contents of which are hereby incorporated by reference in the present disclosure in their entirety.

STATEMENT REGARDING FEDERALLY SPONSORED RESEARCH OR DEVELOPMENT

This invention was made with governmental support through the National Institutes of Health. The Government has certain rights in the invention.

FIELD

This disclosure relates to the identification of ZSCAN4-expressing stem cells and progenitor cells in human pancreas, the use of ZSCAN4 as a marker for pancreatic stem cells and progenitor cells, and the use of such pancreatic stem cells and progenitor cells for treating diabetes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 699442000300SeqList.txt, date recorded: Jul. 22, 2013, size: 51 KB).

BACKGROUND

The Zscan4 gene was identified by expression profiling of all preimplantation stages of mouse embryos using a large-scale cDNA sequencing project (Ko et al., *Development* 127:1737-1749, 2000; Sharov et al., *PLoS Biol* 1:E74, 2003) and DNA microarray analysis (Hamatani et al., *Dev Cell* 6:117-131, 2004). In mice, Zscan4 consists of 6 paralog genes (Zscan4a to Zscan4f) and 3 pseudogenes (Zscan4-ps1 to Zscan4-ps3) clustered on an approximately 850 kb region of chromosome 7. Among the six paralogs, the open reading frames of Zscan4c, Zscan4d, and Zscan4f encode a SCAN domain as well as all four zinc finger domains, suggesting their potential role as transcription factors. A high expression peak of Zscan4 marks the late 2-cell stage of mouse embryos. Zscan4 expression, normally below detection threshold in blastocysts, is reactivated in vitro in a small fraction of ES cells in culture. Although all six Zscan4 paralogs are expressed in ES cells, Zscan4c is the predominant paralog, whereas Zscan4d is the predominant paralog in 2-cell embryos (Falco et al., *Dev Biol* 307:539-550, 2007; PCT Publication No. WO 2008/118957).

It has previously been demonstrated that Zscan4 is associated with a unique transient state in undifferentiated ES cells in which other 2-cell embryo-specific genes are activated. Zscan4 is essential for long-term maintenance of genomic integrity and for mediating a regulated telomere recombination in normal undifferentiated ES cells (Zalzman et al., *Nature* 464(7290):858-863, 2010).

The pancreas has been a focus of intensive research in regenerative medicine because type I diabetes could potentially be cured if insulin-producing pancreatic cells are supplemented. Thus, identifying progenitor cells that could give rise to endocrine and exocrine cells in the adult human pancreas is desirable. The existence of progenitor cells in pancreatic ducts has previously been speculated based on the observation that all pancreatic cells develop from progenitor cells that form duct-like structures in the embryonic pancreas (Oliver-Krasinski and Stoffers, *Genes Dev* 22:1998-2021, 2008). However, little is known about whether undifferentiated progenitor cells exist in pancreatic ducts or if differentiated cells can redifferentiate to other cells types (Aguayo-Mazzucato and Bonner-Weir, *Nat Rev Endocrinol* 6:139-148, 2010). One major hurdle to the identification of resident stem cells in the pancreas is that this tissue type that has a very low rate of spontaneous self-renewal, thus it is expected that the number of pancreatic stems cells, if any, is very low (Barker and Clevers, *Gastroenterology* 138:1681-1696, 2010). Another challenge to identifying resident stem cells is the lack of specific tissue stem cell markers, which has hampered the progress in identifying such a rare cell type in human pancreatic tissues.

SUMMARY

Disclosed herein is the finding that ZSCAN4 serves as a marker for rare stem/progenitor cells in adult human pancreas. Thus, provided herein is a method of isolating pancreatic stem cells or pancreatic progenitor cells, or both, from a sample, such as a pancreatic tissue sample. In some embodiments, the method includes detecting expression of ZSCAN4 in cells of the sample and isolating the cells that express ZSCAN4.

Also provided is a method of treating diabetes in a subject. In some embodiments, the method includes (i) isolating pancreatic stem cells or pancreatic progenitor cells, wherein isolating the pancreatic stem cells or progenitor cells comprises detecting cells in pancreatic tissue that express ZSCAN4; (ii) expanding the isolated pancreatic stem cells or progenitor cells that express ZSCAN4 in vitro; and (iii) transplanting the expanded pancreatic stem cells or progenitor cells into the subject. In particular examples, the pancreatic stem cells or progenitor cells are isolated from the subject to be treated.

Further provided is an in vivo method of expanding a population of pancreatic stem cells or progenitor cells in a subject. In some embodiments, the method includes delivering to the pancreas of the subject a ZSCAN4 protein; a ZSCAN4 nucleic acid sequence; or an agent that increases expression of ZSCAN4 or the number of ZSCAN4+ cells.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SEQUENCE LISTING

Figure 1:
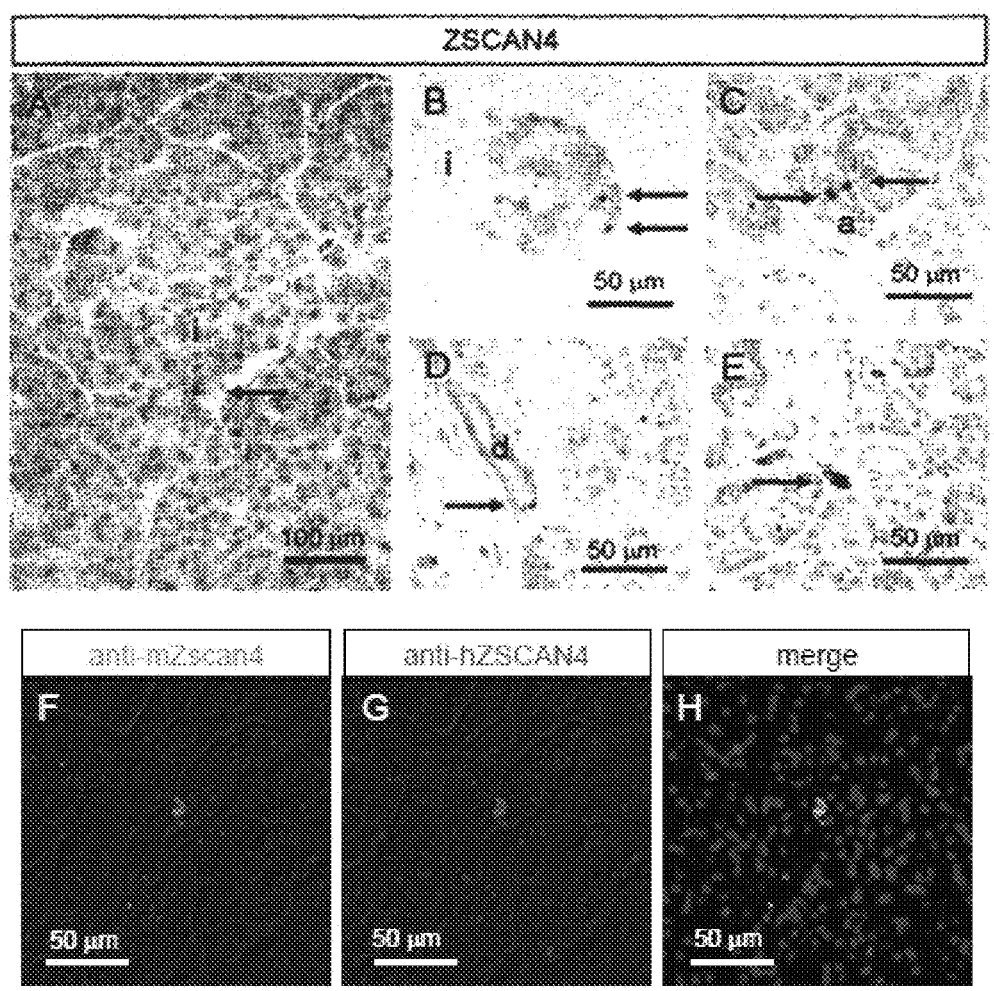
FIGS. 1A-1H are a series of images showing immunolocalization of ZSCAN4 in human pancreas. (A) Existence of a ZSCAN4+ cell in the islet of Langerhans. Strong nuclear staining was observed in this cell. (B) ZSCAN4+ cells are located at the peripheral region of the islet. A weak cytoplasmic staining was evident in endocrine cells. ZSCAN4+ cells are also located in acinus (C) and in the duct (D). Oval-shaped cells ("pancreatic oval cells") are also positive for ZSCAN4 (E). An anti-mouse Zscan4 antibody (F and H) and anti-human ZSCAN4 antibody (G and H) stained identical cells in the human pancreas (oval-shaped cells). i, islet of Langerhans; a, acinus; d, duct.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1 and 2 are nucleotide and amino acid sequences of human ZSCAN4.

SEQ ID NOs: 3 and 4 are nucleotide and amino acid sequences of mouse Zscan4a.

SEQ ID NOs: 5 and 6 are nucleotide and amino acid sequences of mouse Zscan4b.

SEQ ID NOs: 7 and 8 are nucleotide and amino acid sequences of mouse Zscan4c.

SEQ ID NOs: 9 and 10 are nucleotide and amino acid sequences of mouse Zscan4d.

SEQ ID NOs: 11 and 12 are nucleotide and amino acid sequences of mouse Zscan4e.

SEQ ID NOs: 13 and 14 are nucleotide and amino acid sequences of mouse Zscan4f.

SEQ ID NO: 15 is the nucleotide sequence of the Zscan4c promoter-Emerald expression vector (9396 bp). The starting nucleotide of the Zscan4c promoter sequence is 906 and the ending nucleotide is 4468.

DETAILED DESCRIPTION

I. Abbreviations

AQP1 aquaporin 1
BMI1 polycomb ring finger oncogene
CFTR cystic fibrosis transmembrane conductance regulator
ES embryonic stem
FACS fluorescence-activated cell sorting
iPS induced pluripotent stem
LGR5 leucine-rich repeat-containing G-protein-coupled receptor 5
SSEA3 stage-specific embryonic antigen-3

II. Terms and Methods

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject a compound or composition, such as cells that express ZSCAN4, a ZSCAN4 protein or nucleic acid, or an agent that increases expression of ZSCAN4, by any effective route. An exemplary route of administration includes, but is not limited to, injection (such as subcutaneous, intramuscular, intradermal, intraperitoneal, intravenous, intra-arterial or intrapancreatic).

Adult stem cell: Undifferentiated cells found throughout the body after embryonic development that multiply by cell division to replenish dying cells and regenerate damaged tissues. Adult stem cells are also known as somatic stem cells.

Agent: Any protein, nucleic acid molecule, compound, small molecule, organic compound, inorganic compound, or other molecule of interest. In some embodiments, the "agent" is an agent that increases expression of ZSCAN4. In particular examples, the agent is a nucleic acid molecule encoding ZSCAN4 or a retinoid.

Antibiotic resistance gene: Any gene from a microorganism that confers resistance to an antibiotic. In some embodiments, the antibiotic resistance gene confers resistance to puromycin.

Antibody: A polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies) and heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined (see, Kabat et al., *Sequences of Proteins of Immunological Interest*, U.S. Department of Health and Human Services, 1991). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

References to "$V_H$" or "$V_H$" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies. As used herein "monoclonal antibodies" further includes antigen-binding fragments, such as Fv, scFv, dsFv or Fab fragments.

A "chimeric antibody" has framework residues from one species, such as human, and CDRs (which generally confer antigen binding) from another species, such as a murine antibody.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences BMI1 (polycomb ring finger oncogene): A known tissue stem cell marker. BMI1 is necessary for efficient self-renewing cell divisions of adult mouse hematopoietic stem cells (Raaphorst, *Trends Immunol* 24:522-524, 2003). A single BMI1-expressing cell has been shown to form all the cell lineages in the intestinal epithelium (Ootani et al., *Nat Med* 15:701-706, 2009) and BMI1-lineage tracing has identified self-renewing pancreatic acinar cells capable of pancreatic organ homeostasis (Sangiorgi and Capecchi, *Proc Natl Acad Sci USA* 106:7101-7106, 2009).

Contacting: Placement in direct physical association; includes both in solid and liquid form.

Co-expressed: In the context of the present disclosure, genes that are "co-expressed" with ZSCAN4 are genes that exhibit a similar expression pattern as ZSCAN4 during embryonic development, in ES cells, and/or in tissue stem cells, such as pancreatic stem cells or progenitor cells. A number of genes that are co-expressed with ZSCAN4 have been previously described, including AF067063, Tcstv1/3, Tho4, Arginase II, BC061212 and Gm428, Eif1a, EG668777 and Pif1 (see PCT Publication No. WO 2008/118957, which is herein incorporated by reference). In addition, it is disclosed herein (see Example 3) that SSEA3 is co-expressed with ZSCAN4 in pancreatic cells. In particular embodiments disclosed herein, the gene co-expressed with ZSCAN4 is SSEA3 or Tcstv1/3.

Degenerate variant: A polynucleotide encoding a polypeptide, such as a ZSCAN4 polypeptide, that includes a sequence that is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged.

Detectable label: A detectable compound or composition that is conjugated directly or indirectly to another molecule, such as an antibody or a protein, to facilitate detection of that molecule. Specific, non-limiting examples of detectable labels include fluorescent tags, enzymatic linkages, and radioactive isotopes. Various methods of labeling polypeptides and other molecules are known in the art and may be used. Examples of detectable labels for polypeptides include, but are not limited to, the following: radioisotopes or radionucleotides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, chromophores (such as horseradish peroxidase or alkaline phosphatase), biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates.

Diabetes: A disease caused by a relative or absolute lack of insulin leading to uncontrolled carbohydrate metabolism. As used herein, "diabetes" refers to diabetes mellitus. Type 1 diabetes (sometimes referred to as "insulin dependent diabetes" or "juvenile onset diabetes") is an autoimmune disease characterized by destruction of the pancreatic β cells that leads to a total or near total lack of insulin. In diabetes type 2 (sometimes referred to as "non-insulin dependent diabetes" or "adult onset diabetes"), the body does not respond to insulin, though it is present.

Symptoms of diabetes include: excessive thirst (polydipsia); frequent urination (polyuria); extreme hunger or constant eating (polyphagia); unexplained weight loss; presence of glucose in the urine (glycosuria); tiredness or fatigue; changes in vision; numbness or tingling in the extremities (hands, feet); slow-healing wounds or sores; and abnormally high frequency of infection. Diabetes may be clinically diagnosed by a fasting plasma glucose (FPG) concentration of greater than or equal to 7.0 mmol/L (126 mg/dL), or a plasma glucose concentration of greater than or equal to 11.1 mmol/L (200 mg/dL) at about two hours after an oral glucose tolerance test (OGTT) with a 75 g load. A more detailed description of diabetes may be found in *Cecil Textbook of Medicine*, J. B. Wyngaarden, et al., eds. (W.B. Saunders Co., Philadelphia, 1992, 19$^{th}$ ed.).

Differentiation: Refers to the process by which a cell develops into a specific type of cell (for example, muscle cell, pancreatic cell, skin cell etc.). As a cell becomes more differentiated, the cell loses potency, or the ability to become multiple different cell types.

Encapsulated: As used herein, a molecule (such as a nucleic acid or polypeptide) or cell "encapsulated" in a nanoparticle refers to a molecule or cell that is either contained within the nanoparticle or attached to the surface of the nanoparticle, or a combination thereof.

Fluorescent protein: A genetically-encoded protein that exhibits fluorescence when exposed to a particular wavelength of light. A broad range of fluorescent protein genetic variants have been developed that feature fluorescence emission spectral profiles spanning almost the entire visible light spectrum. Examples include anthozoan fluorescent proteins, green fluorescent protein (GFP) (which exhibits green fluorescence when exposed to blue light), as well as mutants thereof such as EGFP, blue fluorescent protein (EBFP, EBFP2, Azurite, mKalamal, which except for mKalamal contain a Y66H substitution.), cyan fluorescent protein (ECFP, Cerulean, CyPet, which include a Y66W substitution), and yellow fluorescent protein derivatives (YFP, Citrin, Venus, YPet, which include a T203Y substitution). Other particular examples include Emerald Green Fluorescent Protein (EmGFP) and Strawberry. For an overview, see Shaner et al., *Nat. Methods* 2(12):905-909, 2005.

Fluorophore: A chemical compound, which when excited by exposure to a particular wavelength of light, emits light (i.e., fluoresces), for example at a different wavelength.

Examples of fluorophores that may be used in the methods disclosed herein are provided in U.S. Pat. No. 5,866,366 to Nazarenko et al.: 4-acetamido-4'-isothiocyanatostilbene-2,2' disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; R-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N', N'-tetramethyl-6-carboxyrhodamine (TAMRA); tetramethyl rhodamine; tetramethyl rhodamine isothiocyanate (TRITC); riboflavin; rosolic acid and terbium chelate derivatives. Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999). Other suitable fluorophores include GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art may also be used, for example those available from Molecular Probes (Eugene, Oreg.).

Heterologous: A heterologous polypeptide or polynucleotide refers to a polypeptide or polynucleotide derived from a different source or species.

Host cell: A cell in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Isolated: An isolated nucleic acid, protein or cell has been substantially separated or purified away from other components with which the nucleic acid, protein or cell naturally occurs. Thus an "isolated" nucleic acid or protein encompasses nucleic acids or proteins purified by standard biochemical purification methods. The term also embraces nucleic acids and proteins prepared by recombinant expression in a host cell as well as chemically synthesized nucleic acids and proteins. Similarly, "isolated" cells, such as those expressing ZSCAN4, have been substantially separated away from other cell types (such as cells that don't express ZSCAN4). In the context of the present disclosure, "isolated" does not require 100% purity of the nucleic acid, protein or cell, but encompasses nucleic acids, proteins and cells that are at least 70%, at least 80%, at least 90%, or at least 95% pure.

LGR5 (leucine-rich repeat-containing G-protein-coupled receptor 5): A stem cell marker of the intestinal epithelium and the hair follicle. The LGR5 protein is expressed in several organs (Barker and Clevers, Gastroenterology 138: 1681-1696, 2010) and genetic marking of LGR5$^+$ cells has identified this membrane protein as a marker for intestinal and skin tissue stem cells in mice (Barker et al., Nature 449:1003-1007, 2007; Snippert et al., *Science* 327:1385-1389, 2010). LGR5 is also known to play a role Wnt signaling. LGR5 sequences are publically available. For example, GenBank Accession Nos. NM_003667 and NP_003658 are human mRNA and protein sequences of LGR5. The NCBI Gene ID for human LGR5 is 8549.

Multipotent cell: Refers to a cell that can form multiple cell lineages, but not all cell lineages.

Nanoparticle: A particle less than about 1000 nanometers (nm) in diameter. Exemplary nanoparticles for use with the methods provided herein are made of biocompatible and biodegradable polymeric materials. In some embodiments, the nanoparticles are PLGA nanoparticles. As used herein, a "polymeric nanoparticle" is a nanoparticle made up of repeating subunits of a particular substance or substances. "Poly(lactic acid) nanoparticles" are nanoparticles having repeated lactic acid subunits. Similarly, "poly(glycolic acid) nanoparticles" are nanoparticles having repeated glycolic acid subunits.

Operably linked: A first nucleic acid sequence is operably linked to a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and where necessary to join two protein coding regions, in the same reading frame.

Pancreas: A nodular organ in the abdomen that contains a mixture of endocrine glands and exocrine glands. The small endocrine portion consists of the islets of Langerhans secreting a number of hormones into the blood stream. The large exocrine portion is a compound acinar gland that secretes several digestive enzymes into the pancreatic ductal system that empties into the duodenum.

Pancreatic beta cell (or β cell): A type of cell in the pancreas found in the islets of Langerhans. Beta cells produce and release insulin, which controls the level of glucose in the blood.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the Zscan4 proteins, Zscan4 nucleic acid molecules, or cells herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

Pharmaceutical agent: A chemical compound, small molecule, cell or other composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Pluripotent cell: A cell that can form all of an organism's cell lineages (endoderm, mesoderm and ectoderm), including germ cells, but cannot form an entire organisms autonomously.

Polynucleotide: A nucleic acid sequence (such as a linear sequence) of at least six nucleotides, such as at least 12, at least 20, at least 30, at least 50, at least 100, at least 1000, or at least 10,000 nucleotides. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide, such as a ZSCAN4. Biologically functional fragments, for example, can vary in size from a polypeptide fragment as small as an epitope capable of binding an antibody molecule to a large polypeptide capable of participating in the characteristic induction or programming of phenotypic changes within a cell, including affecting cell proliferation or differentiation. Thus, smaller peptides containing the biological activity of ZSCAN4, or conservative variants of ZSCAN4, are thus included as being of use.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Examples of conservative substitutions that can be made to a native ZSCAN4 protein (such as SEQ ID NO: 2) are shown below:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Variations in the cDNA sequence that result in amino acid changes, whether conservative or not, should be minimized in order to preserve the functional and immunologic identity of the encoded protein. Thus, in several non-limiting examples, a ZSCAN4 polypeptide, or other polypeptides disclosed herein, includes at most two, at most five, at most ten, at most twenty, or at most fifty conservative substitutions. The immunologic identity of the protein may be assessed by determining whether it is recognized by an antibody; a variant that is recognized by such an antibody is immunologically conserved. Variant amino acid sequences may be, for example, at least 80%, 90% or even 95% or 98% identical to the native amino acid sequence (such as a native ZSCAN4 sequence).

Progenitor cells: Oligopotent or unipotent cells that differentiate into a specific type of cell or cell lineage. Progenitor cells are similar to stem cells but are more differentiated and exhibit limited self renewal.

Promoter: Nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor).

Reporter gene: A gene operably linked to another gene or nucleic acid sequence of interest (such as a promoter sequence). Reporter genes are used to determine whether the gene or nucleic acid of interest is expressed in a cell or has been activated in a cell. Reporter genes typically have easily identifiable characteristics, such as fluorescence, or easily assayed products, such as an enzyme. Reporter genes can also confer antibiotic resistance to a host cell. Exemplary reporter genes include fluorescent and luminescent proteins (such as green fluorescent protein (GFP) and the red fluorescent protein from the gene dsRed), the enzyme luciferase (which catalyzes a reaction with luciferin to produce light), the lacZ gene (which encodes the protein β-galactosidase, which causes cells expressing the gene to appear blue when grown on a medium that contains the substrate analog X-gal), and the chloramphenicol acetyltransferase (CAT) gene (which confers resistance to the antibiotic chloramphenicol). In one embodiment, the reporter gene encodes the fluorescent protein Emerald. In another embodiment, the reporter gene encodes the fluorescent protein Strawberry.

Retinoids: A class of chemical compounds that are related chemically to vitamin A. Retinoids are used in medicine, primarily due to the way they regulate epithelial cell growth. Retinoids have many important and diverse functions throughout the body including roles in vision, regulation of cell proliferation and differentiation, growth of bone tissue, immune function, and activation of tumor suppressor genes. Examples of retinoids include, but are not limited to, all-trans retinoic acid (atRA), 9-cis retinoic acid (9-cis RA), 13-cis RA and vitamin A (retinol).

Sample: A biological specimen containing genomic DNA, RNA (including mRNA), protein, cells, tissue, or combinations thereof, obtained from a subject. Examples include, but are not limited to, peripheral blood, urine, saliva, cerebrospinal fluid, tissue biopsy (such as pancreatic tissue), surgical specimen, and autopsy material. In one example the sample is a human pancreatic tissue sample.

Selectable marker: Refers to a gene that is introduced into a cell that confers a trait that allows for selection or isolation of the cell. Selectable markers include, for example, antibiotic resistance genes.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

One of skill in the art will appreciate that the particular sequence identity ranges are provided for guidance only; it is possible that strongly significant homologs could be obtained that fall outside the ranges provided.

SSEA3 (stage-specific embryonic antigen-3): A molecule that was originally identified by monoclonal antibodies recognizing carbohydrate epitopes. SSEA3 is a known stem cell marker, especially for human pluripotent stem cells (Shevinsky et al., *Cell* 30(3):697-705, 1982; Kannagi et al., *EMBO J.* 2(12):2355-2361, 1983; Kannagi et al., *J Biol Chem* 258(14):8934-8942, 1983).

Stem cell: A cell having the unique capacity to produce unaltered daughter cells (self-renewal; cell division produces at least one daughter cell that is identical to the parent cell) and to give rise to specialized cell types (potency). Stem cells include, but are not limited to, ES cells, EG cells, GS cells, MAPCs, maGSCs, USSCs and adult stem cells. In one embodiment, stem cells can generate a fully differentiated functional cell of more than one given cell type. The role of stem cells in vivo is to replace cells that are destroyed during the normal life of an animal. Generally, stem cells can divide without limit. After division, the stem cell may remain as a stem cell, become a precursor cell, or proceed to terminal differentiation. A precursor cell is a cell that can generate a fully differentiated functional cell of at least one given cell type. Generally, precursor cells can divide. After division, a precursor cell can remain a precursor cell, or may proceed to terminal differentiation.

Subject: Living multi-cellular vertebrate organisms, a category that includes human and non-human mammals.

Tcstv1/3 (two-cell stage, variable group, members 1 and 3): A gene that has previously been shown to co-express with ZSCAN4 (PCT Publication No. WO 2008/118957). Tcstv1 and Tcstv3 are splice variants.

Therapeutic amount: An amount of a therapeutic agent sufficient to achieve the intended purpose. For example, a therapeutic amount of ZSCAN4$^+$ pancreatic stem cells or progenitor cells is an amount sufficient to reduce a disorder or symptoms of a disorder that can benefit from such therapy, such as diabetes. A therapeutic amount may in some examples not treat the disorder or symptoms 100%. However, a decrease in any known feature or symptom of a disorder that can benefit from administration of the therapeutic agent, such as a decrease of at least 10%, at least 15%, at least 25%, at least 30%, at least 50%, at least 60%, at least 70%, at least 75%, at least 85%, at least 95%, or greater, can be therapeutic. The therapeutic amount of a given therapeutic agent will vary with factors such as the nature of the agent, the route of administration, the size and species of the animal to receive the therapeutic agent, and the purpose of the administration. The therapeutic amount in each individual case can be determined empirically without undue experimentation by a skilled artisan according to established methods in the art.

Totipotent cell: Refers to a cell that can form an entire organism autonomously. Only a fertilized egg (oocyte) possesses this ability (stem cells do not).

Transfecting or transfection: Refers to the process of introducing nucleic acid into a cell or tissue. Transfection can be achieved by any one of a number of methods, such as, but not limited to, liposomal-mediated transfection, electroporation and injection.

Transplanting: Refers to the process of grafting an organ, tissue or cells into a subject.

Vector: A nucleic acid molecule as introduced into a host cell, thereby producing a transformed host cell. A vector may include nucleic acid sequences that permit it to replicate in a host cell, such as an origin of replication (DNA sequences that participate in initiating DNA synthesis). For example, an expression vector contains the necessary regulatory sequences to allow transcription and translation of inserted gene or genes. A vector may also include one or more selectable marker genes and other genetic elements known in the art. Vectors include, for example, virus vectors and plasmid vectors.

ZSCAN4: A group of genes that have previously identified as exhibiting 2-cell-specific expression and ES cell-specific expression (PCT Publication No. WO 2008/118957) and have been shown to promote telomere elongation and genome stability (Zalzman et al., Nature 464(7290):858-863, 2010). In the context of the present disclosure, "ZSCAN4" includes both human ZSCAN4 and mouse Zscan4. In the mouse, the term "Zscan4" refers to a collection of genes including three pseudogenes (Zscan1-ps1, Zscan4-ps2 and Zscan4-ps3) and six expressed genes (Zscan4a, Zscan4b, Zscan4c, Zscan4d, Zscan4e and Zscan4f). ZSCAN4 refers to ZSCAN4 polypeptides and ZSCAN4 polynucleotides encoding the ZSCAN4 polypeptides. Exemplary sequences are provided herein.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein, including GenBank accession numbers, are incorporated by reference in their entirety. In case of conflict, the present specification, including explanations of terms, will control. In addition, the materials, methods, and examples are illustrative only and not intended to be limiting.

III. Overview of Several Embodiments

The lack of appropriate markers has prevented the identification and isolation of stem cells and progenitor cells in the adult pancreas. It has previously been disclosed that Zscan4, a gene intermittently expressed in murine embryonic stem (ES) cells, regulates telomere elongation and genome stability in these cells. It is disclosed herein that in the adult human pancreas, a small number of ZSCAN4-positive cells are present among cells located in the islets of Langerhans, acini, and ducts. It was also determined that ZSCAN4 is expressed in some of the oval-shaped cells located in the interstitium between acini, where pancreatic stellate cells are also located. In many cases, these ZSCAN4-positive cells were also positive for other tissue stem cell markers such as BMI1 and LGR5. Furthermore, the number of ZSCAN4-positive cells dramatically increased in patients with chronic pancreatitis, especially in the pancreatic tissues actively regenerating after corticosteroid treatment. However, a year after the treatment, the number of ZSCAN4-positive cells returned to very low levels—comparable to that of the unaffected pancreas. The data disclosed herein indicate that the expression of ZSCAN4 serves as a biomarker for rare stem/progenitor cells in adult human pancreas.

Accordingly, provided herein is a method of isolating pancreatic stem cells or pancreatic progenitor cells, or both, from a sample, such as a pancreatic tissue sample. In some embodiments, the method includes detecting expression of ZSCAN4 in cells of the sample and isolating the cells that express ZSCAN4.

Also provided is a method of treating a subject with a disease or disorder of the pancreas. The disease or disorder of the pancreas can be associated with the endocrine function of the pancreas or the exocrine function of the pancreas. In some cases, the disease or disorder associated with the endocrine function of the pancreas is diabetes. Thus, provided herein is a method of treating diabetes in a subject. In some embodiments, the method includes (i) isolating pancreatic stem cells or pancreatic progenitor cells, wherein isolating the pancreatic stem cells or progenitor cells comprises detecting cells in pancreatic tissue that express ZSCAN4; (ii) expanding the isolated pancreatic stem cells or progenitor cells that express ZSCAN4 in vitro; and (iii) transplanting the expanded pancreatic stem cells or progenitor cells into the subject. In particular examples, the pancreatic stem cells or progenitor cells are isolated from the subject to be treated.

Further provided is an in vivo method of expanding a population of pancreatic stem cells or progenitor cells in a subject. In some embodiments, the method includes delivering to the pancreas of the subject a ZSCAN4 protein; a ZSCAN4 nucleic acid sequence; or an agent that increases expression of ZSCAN4 or increases the number of ZSCAN4$^+$ cells.

Also provided are screening assays to identify agents that stimulate pancreatic stem cells to regenerate exocrine and endocrine cells (including insulin-secreting pancreatic beta cells) by identifying agents that increase expression of ZSCAN4.

A. Methods of Isolating Pancreatic Stem Cells and Progenitor Cells

Provided herein is a method of isolating pancreatic stem cells or pancreatic progenitor cells, or both, from a sample. In some embodiments, the method includes detecting expression of ZSCAN4 (such as detecting the presence of a sequence having at least 80%, at least 85%, at least 90%, at least 95%, at least 96%, at least 97%, at least 98% or at least 99% sequence identity to the sequence set forth as SEQ ID NO: 2) in cells of the sample and isolating the cells that express ZSCAN4. In particular examples, the sample comprises human pancreatic tissue.

In some embodiments of the disclosed methods, detecting expression of ZSCAN4 includes detecting expression of a gene that is co-expressed with ZSCAN4. Described herein is the finding that SSEA3, a known stem cell marker, exhibits a similar expression pattern as ZSCAN4 in pancreatic tissue (see FIG. 11). Thus, in particular examples, the gene that is co-expressed with ZSCAN is SSEA3. Other genes have been identified as co-expressed with ZSCAN4. For example, PCT Publication No. WO 2008/118957 discloses that AF067063, Tcstv1/3, Tho4, Arginase 11, BC061212 and Gm428, Eif1a, EG668777 and Pif1 are co-expressed genes. Thus in some embodiments, the gene that is co-expressed with ZSCAN4 is selected from the group consisting of AF067063, Tcstv1/3, Tho4, Arginase 11, BC061212 and Gm428, Eif1a, EG668777 and Pif1. In one non-limiting example, the gene that is co-expressed with ZSCAN4 is Tcstv1/3.

The co-expressed gene need not exhibit an identical expression pattern to ZSCAN4 but generally exhibits an expression pattern that is very similar to ZSCAN4 such that the majority of cells (such as at least about 70%, at least about 75%, at least about 80%, at least about 85%, at least about 90%, or at least about 95%) that are isolated by detecting the ZSCAN4 co-expressed gene also express ZSCAN4.

In some embodiments, the gene that is co-expressed with ZSCAN4 encodes a membrane protein to facilitate antibody-based detection of the protein.

In some embodiments, detecting expression of ZSCAN4 comprises contacting the sample with an antibody specific for a protein encoded by ZSCAN4 or an antibody specific for a protein encoded by a gene co-expressed with ZSCAN4. In particular examples, the antibody is specific for a protein encoded by ZSCAN4. In other examples, the antibody is specific for a protein encoded by SSEA3. In yet other examples, the antibody is specific for a protein encoded by Tcstv1/3. Antibodies specific for proteins encoded by ZSCAN4, SSEA3 and Tcstv1/3 are commercially available and/or can be generating using methods well known to one of skill in the art (see Table 1 for examples of ZSCAN4 antibodies).

Antibody-mediated detection and isolation methods are well known to those of skill in the art. In some cases, the antibody specific for ZSCAN4, or a gene product encoded by a gene co-expressed with ZSCAN4, is bound to a detectable label, such as a fluorophore. Thus, in particular embodiments, a ZSCAN4-specific antibody conjugated to a fluorophore is contacted with cells of the sample. ZSCAN4$^+$ cells will bind the antibody and can be isolated, for example, by fluorescence activated cell sorting (FACS). Similarly, fluorophore-conjugated antibodies specific for gene products of ZSCAN4 co-expressed genes can be contacted with cells of the sample to isolate cells that express the ZSCAN4 co-expressed gene, thereby isolating ZSCAN4$^+$ cells. Antibodies can also be conjugated to other detectable markers, such as magnetic beads (to allow for magnetic separation of ZSCAN4$^+$ cells).

In other embodiments, detecting expression of ZSCAN4 comprises transfecting the cells of the sample with a vector comprising a ZSCAN4 promoter operably linked to a heterologous nucleic acid sequences, such as a reporter gene or a selectable marker. The heterologous nucleic acid sequence can encode any type of molecule that allows for detection and/or selection of cells that express ZSCAN4. In some examples, the heterologous nucleic acid sequence is a reporter gene. The reporter gene can be, for example, a fluorescent protein or enzyme. In particular non-limiting examples, the fluorescent protein is GFP, or a derivative thereof, such as Emerald. Use of a fluorescent maker allows for isolation of cells using, for example, FACS.

In other examples, the heterologous nucleic acid molecule is a selectable marker. In some examples, the selectable marker is an antibiotic resistance gene. Suitable antibiotic resistance genes include, but are not limited to, genes that confer resistance to puromycin, blasticidin, hygromycin, gentamicin, G418 and the like. One of skill in the art can readily choose an appropriate selectable marker for mammalian cells and the corresponding antibiotic to select cells that express ZSCAN4. If the vector includes an antibiotic resistance gene, cells transfected with the vector can be cultured in the presence of the corresponding antibiotic. Cells that express ZSCAN4 will also express the antibiotic resistance gene and survive in the presence of the antibiotic; cells that do not express ZSCAN4 will die, thereby allowing for isolation of ZSCAN4$^+$ cells.

In some embodiments, the promoter comprises at least a portion of the human ZSCAN4 promoter. In particular examples, the promoter comprises the human ZSCAN4 promoter. In other embodiments, the ZSCAN4 promoter comprises at least a portion of the mouse Zscan4c promoter. In particular examples, the Zscan4c promoter comprises the nucleic acid sequence set forth as nucleotides 906-4468 of SEQ ID NO: 15. In some embodiments, the vector for detection of ZSCAN4$^+$ cells comprises a nucleic acid sequence having at least 80%, at least 85%, at least 90%, at least 95%, at least 96%, at least 97%, at least 98% or at least 99% sequence identity to the sequence set forth as SEQ ID NO: 15, and in some examples comprises SEQ ID NO: 15.

In some embodiments disclosed herein, the method further includes detecting expression of a known tissue stem cell marker, such as, but not limited LGR5 or BMI1. Thus, in particular examples, the method further includes detecting expression of LGR5 or BMI1, or both, and isolating cells that also express LGR5 or BMI1, or both.

B. Methods of Treating a Disease or Disorder of the Pancreas

Also provided herein is a method of treating a subject with a disease or disorder of the pancreas. The disease or disorder of the pancreas can be associated with the endocrine function of the pancreas or the exocrine function of the pancreas. In some cases, the disease or disorder associated with the endocrine function of the pancreas is diabetes.

Transplantation of insulin-producing islet cells, or pancreatic stem/progenitor cells capable of differentiation into such cells, isolated in vitro from a donor pancreas has the potential to cure type 1 and some cases of type 2 diabetes (Serup et al., *BMJ* 322:29-32, 2001). However, a lack of sufficient donor cells, and the side effects of immunosuppressive therapy required to successfully transplant allogeneic cells into a subject in need of therapy, have limited the potential of this treatment option. The methods disclosed herein for isolating pancreatic stem cells and progenitor cells provide a means for overcoming these difficulties.

Provided herein is a method of treating diabetes in a subject. In some embodiments, the method includes (i) isolating pancreatic stem cells or pancreatic progenitor cells, wherein isolating the pancreatic stem cells or progenitor cells includes detecting cells in pancreatic tissue that express ZSCAN4 (such as a ZSCAN4 sequence having at least 80%, at least 85%, at least 90%, at least 95%, at least 96%, at least 97%, at least 98% or at least 99% sequence identity to the sequence set forth as SEQ ID NO: 2); (ii) expanding the isolated pancreatic stem cells or progenitor cells that express ZSCAN4 in vitro; and (iii) transplanting the expanded pancreatic stem cells or progenitor cells into the subject. In particular examples, the pancreatic stem cells or progenitor cells are isolated from the subject to be treated. In some embodiments, the method further includes selecting a subject in need of treatment, such as a subject that has been diagnosed with diabetes (including type 1 or type 2 diabetes).

The pancreatic tissue can be obtained from the subject to be treated or from a donor subject using standard methods, such as by surgery or biopsy. Biopsies of the pancreas can be performed according to any standard method, such as fine needle aspiration (FNA), core biopsy or laparoscopy (Paulsen et al., *Interventional Radiology* 187:769-772, 2006; Freeny et al., *West J Med* 132:283-287, 1980). In particular examples, pancreatic tissue is obtained using a 19-gauge TRU-CUT™ biopsy needle under visual guidance of endoscopic ultrasonography.

In some embodiments, the method further includes differentiating the pancreatic stem cells or progenitor cells into pancreatic β cells before transplanting the cells into the subject. Methods of culturing pancreatic cells and differentiating pancreatic stem cells or progenitor cells (such as into cells) in vitro has been described (see, for example, Ramiya et al., *Nat Med* 6:278-282, 2000; Bonner-Weir et al., *Proc Natl Acad Sci USA* 97(14):7999-8004, 2000; U.S. Patent Application Publication Nos. 2005/0069529 and 2008/0274090).

Transplantation of the pancreatic cells (stem cell, progenitor cells or differentiated cells) into the subject in need of treatment can be accomplished using any suitable method known in the art. In some embodiments, the pancreatic cells are delivered by direct injection into the pancreas. As one example, the pancreatic cells can be transplanted by puncturing the kidney capsule with a hypodermic needle, threading a thin capillary tube through the puncture site into the kidney and injecting the cells into the cortex region of the pancreas (such as is described in U.S. Patent Application Publication No. 2008/0274090). In another example, pancreatic cells are transplanted by placing a catheter through the upper abdomen and into the portal vein of the liver. Pancreatic cells are then slowly infused into the liver.

In some embodiments, the expanded pancreatic stem cells, progenitor cells or β cells are administered alone, in the presence of a pharmaceutically acceptable carrier (such as encapsulated in a suitable polymer) or in the presence of other therapeutic agents.

In one example, the pancreatic cells are encapsulated into a semipermeable polymer membrane and the polymer membrane transplanted into the diabetic subject (see U.S. Pat. No. 5,573,528 for description of encapsulation of compounds and cells).

The semipermeable polymer membrane can be synthetic or natural. Examples of polymer that can be used include polyethersulfone (PES), polyacrylonitrile-co-vinyl chloride (P[AN/VC], poly(lactic acid), poly(lactic-co-glycolic acid), methylcellulose, hyaluronic acid, collagen, and the like. Delivery of encapsulated pancreatic cells within a polymer membrane can avoid host rejection and immune response to cells, and problems associated with rejection and inflammation. In addition, cells contained within the polymer membrane are shielded by the wall of the polymer (i.e., the walls of the individual fibers, fibrils, films, sprays, droplets, particles, etc.) from immune surveillance while still maintaining cell viability and allowing transport of molecules, nutrients and metabolic products through the polymer walls. The grafting of polymer-encapsulated cells has been developed by Aebischer et al. (*Transplant*, 111:269-275, 1991) and has been successfully used with both non-human primates and humans (Aebischer et al., 1994, *Transplant*, 58:1275-1277; U.S. Pat. No. 6,110,902).

In one example, the expanded pancreatic cells are encapsulated by first embedding them into a matrix of either collagen, agarose or PVA (polyvinylalcohol). Subsequently, the embedded cells are injected into hollow fibers made of polypropylene of a 60:40 copolymer of polyacrylnitrile:polyvinylchloride. The fibers are cut into pieces and end-sealed for implantation.

C. Methods of Expanding Pancreatic Stem/Progenitor Cells In Vivo

Further provided herein is an in vivo method of expanding a population of pancreatic stem cells or progenitor cells in a subject. In some embodiments, the method includes delivering to the pancreas of the subject a ZSCAN4 protein; a ZSCAN4 nucleic acid sequence; or an agent that increases expression of ZSCAN4 or increases the number of ZSCAN4$^+$ cells. In some embodiments, the method further includes selecting a subject in need of expansion of pancreatic stem cells or progenitor cells. For example, the subject can be a subject with diabetes.

In some embodiments, the ZSCAN4 protein or nucleic acid sequences is a human ZSCAN4 protein or nucleic acid sequence. In other embodiments, the ZSCAN4 protein or nucleic acid sequence is a murine Zscan4 sequence.

In some embodiments, the amino acid sequence of the ZSCAN4 protein is at least 80%, at least 85%, at least 90%, at least 95%, at least 96%, at least 97%, at least 98% or at least 99% identical to the amino acid sequence of SEQ ID NO: 2. In some examples, the ZSCAN4 protein comprises the amino acid sequence of SEQ ID NO: 2. In particular non-limiting examples, the ZSCAN4 protein consists of the amino acid sequence of SEQ ID NO: 2. In other examples, the ZSCAN4 protein comprises a functional fragment of SEQ ID NO: 2 or a conservative variant of SEQ ID NO: 2.

In some embodiments, the ZSCAN4 nucleic acid sequence is at least 80%, at least 85%, at least 90%, at least 95%, at least 96%, at least 97%, at least 98% or at least 99% identical to the nucleic acid sequence of SEQ ID NO: 1. In some examples, the ZSCAN4 nucleic acid sequence comprises the nucleotide sequence of SEQ ID NO: 1. In particular non-limiting examples, the ZSCAN4 nucleic acid sequence consists of the nucleotide sequence of SEQ ID NO: 1. In other examples, the ZSCAN4 nucleic acid sequence encodes a functional fragment or a conservative variant of the ZSCAN4 protein of SEQ ID NO: 2.

In some embodiments, delivery of the ZSCAN4 nucleic acid sequence includes administration of a vector that comprises the ZSCAN4 nucleic acid sequence. Methods of generating and using ZSCAN4-expressing vectors are described in other sections of the application.

In some embodiments, delivery of the ZSCAN4 protein or the ZSCAN4 nucleic acid sequence (such as a vector comprising a ZSCAN4 nucleic acid sequence) includes administration of a ZSCAN4 protein or nucleic acid encapsulated by a nanoparticle. Methods of delivering proteins and nucleic acid molecules using nanoparticles are well known in the art and are described below in section V.D.

The inventors have previously demonstrated that retinoids can transiently increase Zscan4$^+$ cells in mouse ES cell culture (PCT/US2010/047644, filed Sep. 2, 2010). Thus, in some embodiments, the agent that increases expression of ZSCAN4 is a retinoid. Exemplary retinoids include, but are not limited to atRA, 9-cis RA, 13-cis RA and vitamin A.

Delivery of the ZSCAN4 protein, ZSCAN4 nucleic acid, or agent that increases expression of ZSCAN4 (or increases the number of ZSCAN4+ cells) can be accomplished using any suitable method known in the art and will vary depending upon the molecule or composition to be delivered. In some embodiments, the ZSCAN4 protein, ZSCAN4 nucleic acid, or agent that increases expression of ZSCAN4 or increases the number of ZSCAN4+ cells is delivered to the pancreas of the subject by injection. In other embodiments, the agent is injected into the local or systemic blood circulation to allow for delivery of the agent to the pancreas. In yet other embodiments, the agent is administered orally.

D. Screening Assays

Further provided herein are screening assays to identify agents that stimulate pancreatic stem cells to regenerate exocrine and endocrine cells (including insulin-secreting pancreatic beta cells) by identifying agents that increase expression of ZSCAN4 or increase the number of ZSCAN4+ cells in a given population of cells (such as cells in the pancreas). In some embodiments, the method includes contacting a cell culture with a candidate agent and detecting expression of ZSCAN4. An increase in expression of ZSCAN4 following addition of the agent to the cell culture relative to a control, indicates the agent is capable of stimulating pancreatic stem cells to regenerate exocrine and endocrine cells. The control can be, for example, the level of ZSCAN4 expression prior to addition of the agent, expression of ZSCAN4 in a control cell culture, or a reference value, such as a value that is representative of ZSCAN4 expression in a similar cell culture in the absence of an exogenous agent.

In some embodiments, the cell culture comprises pancreatic cells, such as primary pancreatic cells, or cells of a pancreatic cell line. In other embodiments, the cell culture comprises pluripotent stem cells, such as embryonic stem cells.

In some embodiments, the assay includes detecting expression of ZSCAN4 mRNA, such as by PCR. In other embodiments, the assay includes detecting expression of ZSCAN4 protein, such as by ELISA. In yet other embodiments, the assay includes detecting expression of a reporter (such as GFP) under the control of a ZSCAN4 promoter.

Agents that are identified using the disclosed screening assays can be used, for example, to administer to a subject in order to expand pancreatic stem/progenitor cells in vivo.

IV. Zscan4 Promoter Sequences and Expression Vectors

Expression vectors comprising a ZSCAN4 promoter and a reporter gene have been previously described (see PCT Publication No. WO 2008/118957). An expression vector comprising a ZSCAN4 promoter sequence operably linked to a nucleic acid sequence encoding a heterologous polypeptide (such as a reporter gene or selectable marker) can be used to identify cells that express ZSCAN4. Methods of detecting expression of the reporter gene, and thus the ZSCAN4+ cells, vary depending upon the type of reporter gene, but are well known in the art. For example, when a fluorescent reporter is used, detection of expression can be achieved by FACS or fluorescence microscopy. In other examples, when a selectable marker is used, such as an antibiotic resistance gene, the cells are incubated in the presence of an appropriate selection agent (such as antibiotic), which will kill all cells that do not express ZSCAN4.

In some examples a heterologous nucleic acid sequence (such as a reporter molecule) is expressed under the control of a ZSCAN4 promoter (for example in a vector). In some embodiments, the ZSCAN4 promoter is the mouse Zscan4c promoter. For example, the Zscan4c promoter can include the nucleic acid sequence set forth as nucleotides 906-4468 of SEQ ID NO: 15. In some examples, the Zscan4c promoter comprises Zscan4c exon and/or intron sequence. Other expression control sequences, including appropriate enhancers, transcription terminators, a start codon (i.e., ATG) in front of a protein-encoding gene, splicing signals for introns, and stop codons can be included with the ZSCAN4 promoter in an expression vector. Generally the promoter includes at least a minimal sequence sufficient to direct transcription of a heterologous nucleic acid sequence. In several examples, the heterologous nucleic acid sequence encodes a reporter molecule or a selectable marker (such as an antibiotic resistance gene).

The heterologous protein encoded by the heterologous nucleic acid sequence is typically a reporter molecule or selectable maker, such as a marker, an enzyme, a fluorescent protein, a polypeptide that confers antibiotic resistance to the cell, or an antigen that can be identified using conventional molecular biology procedures. Reporter molecules can be used to identify a cell, or a population of cells, of interest, such as ZSCAN4+ pancreatic cells. In one embodiment, the heterologous protein is a fluorescent marker (such as a green fluorescent protein, or a variant thereof, e.g. Emerald (Invitrogen, Carlsbad, Calif.)) an antigenic marker (such as human growth hormone, human insulin, human HLA antigens); a cell-surface marker (such as CD4, or any cell surface receptor); or an enzymatic marker (such as lacZ, alkaline phosphatase). Expression of the reporter gene indicates the cell expresses Zscan4. Methods of detecting expression of the reporter gene vary depending upon the type of reporter gene and are well known in the art. For example, when a fluorescent reporter is used, detection of expression can be achieved by FACS or fluorescence microscopy.

In another embodiment, the heterologous protein confers antibiotic resistance, such as resistance to puromycin. Thus, the cells are incubated in the presence of the appropriate antibiotic (such as puromycin) to select for cells that express ZSCAN4.

Expression vectors typically contain an origin of replication as well as specific genes which allow phenotypic selection of the transformed cells. Vectors suitable for use are well known in the art, including viral vectors and plasmid vectors (including those described in Section V below). In one example, an enhancer is located upstream of the ZSCAN4 promoter, but enhancer elements can generally be located anywhere on the vector and still have an enhancing effect. However, the amount of increased activity will generally diminish with distance. Additionally, two or more copies of an enhancer sequence can be operably linked one after the other to produce an even greater increase in promoter activity.

Expression vectors including a ZSCAN4 promoter can be used to transform host cells, such as, but not limited to pancreatic cells. Biologically functional viral and plasmid DNA vectors capable of expression and replication in a host are known in the art, and can be used to transfect any cell of interest.

A "transfected cell" is a host cell into which (or into an ancestor of which) has been introduced a nucleic acid molecule (e.g., DNA molecule), such as a DNA molecule including a ZSCAN4 promoter element. Transfection of a host cell with a recombinant nucleic acid molecule may be carried out by conventional techniques as are well known to those skilled in the art. As used herein, transfection includes liposomal-mediated transfection, electroporation, injection or any other suitable technique for introducing a nucleic acid molecule into a cell.

V. Zscan4 Polynucleotide and Polypeptide Sequences

ZSCAN4 nucleic acid and amino acid sequences have been previously described in the art (see, for example, WO 2008/118957, the disclosure of which is herein incorporated by reference; Falco et al., *Dev. Biol.* 307(2):539-550, 2007; and Carter et al., *Gene Expr. Patterns.* 8(3):181-198, 2008). As used herein, the term "ZSCAN4" includes human ZSCAN4, any one of a group of mouse genes exhibiting 2-cell embryonic stage- or ES cell-specific expression (including Zscan4a, Zscan4b, Zscan4c, Zscan4d, Zscan4e and Zscan4f), or any other species ortholog of ZSCAN4.

A. ZSCAN4 Amino Acid Sequences

Exemplary ZSCAN4 amino acid sequences are set forth in the Sequence Listing as SEQ ID NO: 2 (human ZSCAN4), SEQ ID NO: 4 (Zscan4a), SEQ ID NO: 6 (Zscan4b), SEQ ID NO: 8 (Zscan4c), SEQ ID NO: 10 (Zscan4d), SEQ ID NO: 12 (Zscan4e) and SEQ ID NO: 14 (Zscan4f). One skilled in the art will appreciate that sequences having at least 80%, at least 90%, at least 95%, or at least 98% sequence identity to these sequences and retain ZSCAN4 activity (such as the ability to enhance genome stability and increase telomere length in a ES cell) can be used in the methods provided herein.

ZSCAN4 amino acid sequences from other species are publically available, including dog ZSCAN4 (GenBank Accession Nos. XP_541370 and XP_853650); cow ZSCAN4 (GenBank Accession No. XP_001789302); and horse ZSCAN4 (GenBank Accession No. XP_001493994). Each of the above-listed GenBank Accession numbers is herein incorporated by references as it appears in the GenBank database on Jan. 14, 2011.

Specific, non-limiting examples of ZSCAN4 polypeptides that can be expressed in cells (such as pancreatic cells), or delivered in vivo (such as to the pancreas) according to the methods provided herein include polypeptides having an amino acid sequence at least 80%, at least 85%, at least 90%, at least 95%, at least 96%, at least 97%, at least 98% or at least 99% homologous to the amino acid sequence set forth in SEQ ID NO: 2, 4, 6, 8, 10, 12 or 14. In a further embodiment, a ZSCAN4 polypeptide is a conservative variant of SEQ ID NO: 2, 4, 6, 8, 10, 12 or 14, such that it includes no more than fifty conservative amino acid substitutions, such as no more than two, no more than five, no more than ten, no more than twenty, or no more than fifty conservative amino acid substitutions in SEQ ID NO: 2, 4, 6, 8, 10, 12 or 14. In another embodiment, a ZSCAN4 polypeptide has an amino acid sequence comprising the amino acid sequence set forth in SEQ ID NO: 2, 4, 6, 8, 10, 12 or 14. In another embodiment, a ZSCAN4 polypeptide has an amino acid sequence consisting of the amino acid sequence set forth in SEQ ID NO: 2, 4, 6, 8, 10, 12 or 14.

Fragments and variants of a ZSCAN4 polypeptide can readily be prepared by one of skill in the art using molecular techniques. In one embodiment, a fragment of a ZSCAN4 polypeptide includes at least 50, at least 100, at least 150, at least 200, at least 250, at least 300, at least 350, at least 400, at least 450 or at least 500 consecutive amino acids of the ZSCAN4 polypeptide. In a further embodiment, a fragment of ZSCAN4 is a fragment that confers a function of ZSCAN4 when transferred into a cell of interest.

Minor modifications of the ZSCAN4 polypeptide primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein.

One of skill in the art can readily produce fusion proteins including a ZSCAN4 polypeptide and a second polypeptide of interest. Optionally, a linker can be included between the ZSCAN4 polypeptide and the second polypeptide of interest. Fusion proteins include, but are not limited to, a polypeptide including a ZSCAN4 polypeptide and a marker protein. In one embodiment, the marker protein can be used to identify or purify a ZSCAN4 polypeptide. Exemplary fusion proteins include, but are not limited to, green fluorescent protein, six histidine residues, or myc and a ZSCAN4 polypeptide.

One skilled in the art will appreciate that such variants, fragments, and fusions of Zscan4 useful for the disclosed methods are those that retain ZSCAN4 activity.

B. ZSCAN4 Nucleic Acid Sequences

Nucleic acid molecules encoding a Zscan4 polypeptide are termed Zscan4 polynucleotides or nucleic acid molecules. These polynucleotides include DNA, cDNA and RNA sequences which encode a ZSCAN4 protein. It is understood that all polynucleotides encoding a ZSCAN4 polypeptide are also included herein, as long as they encode a polypeptide with a recognized ZSCAN4 activity, such as the ability to modulate genome stability or telomere length in an ES cell. The polynucleotides include sequences that are degenerate as a result of the genetic code. There are 20 natural amino acids, most of which are specified by more than one codon. Therefore, all degenerate nucleotide sequences are included as long as the amino acid sequence of the ZSCAN4 polypeptide encoded by the nucleotide sequence is functionally unchanged. A ZSCAN4 polynucleotide encodes a ZSCAN4 polypeptide, as disclosed herein. Exemplary polynucleotide sequences encoding ZSCAN4 that can be expressed in cells, or delivered to cells or tissues, using the methods provided herein are set forth in the Sequence Listing as SEQ ID NO: 1 (human ZSCAN4), SEQ ID NO: 3 (Zscan4a), SEQ ID NO: 5 (Zscan4b), SEQ ID NO: 7 (Zscan4c), SEQ ID NO: 9 (Zscan4d), SEQ ID NO: 11 (Zscan4e), and SEQ ID NO: 13 (Zscan4f).

ZSCAN4 nucleic acid sequences from other species are publically available, including dog ZSCAN4 (GenBank Accession Nos. XM_541370 and XM_848557); cow ZSCAN4 (GenBank Accession No. XM_001789250); and horse ZSCAN4 (GenBank Accession No. XM_001493944). Each of the above-listed GenBank Accession numbers is herein incorporated by references as it appears in the GenBank database on Jan. 14, 2011.

In some embodiments, the ZSCAN4 polynucleotide sequence expressed in or delivered to a cell (such as a pancreatic cell) according to the methods provided herein is at least 80%, at least 85%, at least 90%, at least 95%, at least 96%, at least 97%, at least 98% or at least 99% identical to SEQ ID NO: 1, 3, 5, 7, 9, 11 or 13. In some embodiments, the ZSCAN4 polynucleotide sequence comprises the nucleic acid sequence set forth in SEQ ID NO: 1, 3, 5, 7, 9, 11 or 13. In some embodiments, the Zscan4 polynucleotide sequence consists of the nucleic acid sequence set forth in SEQ ID NO: 1, 3, 5, 7, 9, 11 or 13.

Fragments and variants of ZSCAN4 polynucleotides can readily be prepared by one of skill in the art using molecular techniques. In one embodiment, a fragment of a ZSCAN4 polynucleotide includes at least 250, at least 500, at least 750, at least 1000, at least 1500, or at least 2000 consecutive nucleic acids of the ZSCAN4 polynucleotide. In a further embodiment, a fragment of ZSCAN4 is a fragment that confers a function of ZSCAN4 when expressed in a cell of interest.

Minor modifications of the ZSCAN4 polynucleotide sequences may result in expression of peptides which have substantially equivalent activity as compared to the unmodified counterpart polynucleotides described herein. Such modifications may be deliberate, as by site-directed mutagenesis, or may be spontaneous. All of the polynucleotides produced by these modifications are included herein.

C. Vectors Encoding ZSCAN4

ZSCAN4 polynucleotides include recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

With the provision of several ZSCAN4 nucleic acid and protein sequences described above, the expression of any ZSCAN4 protein (e.g., a heterologous ZSCAN4 protein) in cell (such as a pancreatic cell) using standard laboratory techniques is enabled. In some examples, the ZSCAN4 nucleic acid sequence is under the control of a promoter. In some examples, a vector system is used to express ZSCAN4, such as plasmids, bacteriophages, cosmids, animal viruses and yeast artificial chromosomes (YACs). These vectors may then be introduced into pancreatic cells.

A ZSCAN4 coding sequence may be operably linked to a heterologous promoter, to direct transcription of the ZSCAN4 coding nucleic acid sequence. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. In one example, the promoter is a constitutive promoter, such as the CAG-promoter (Niwa et al., Gene 108(2):193-9, 1991), or the phosphoglycerate kinase (PGK)-promoter. In another example, the promoter is an inducible promoter such as a tetracycline-inducible promoter (Masui et al., Nucleic Acids Res. 33:e43, 2005). Other exemplary promoters that can be used to drive ZSCAN4 expression include but are not limited to: lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, and the promoter of the yeast alpha-mating factors. In some examples, a native ZSCAN4 promoter is used.

A vector system can used to express ZSCAN4. Exemplary vectors that can be used to express Zscan4 in cells include but are not limited to plasmids and viral vectors. In one example, vectors containing the promoter and enhancer regions of the SV40 or long terminal repeat (LTR) of the Rous Sarcoma virus and polyadenylation and splicing signal from SV40 (Mulligan and Berg, 1981, Proc. Natl. Acad. Sci. USA 78:2072-6; Gorman et al., 1982, Proc. Natl. Acad. Sci. USA 78:6777-81) are used. In one example, the vector is a viral vector, such as an adenoviral vector, an adeno-associated virus (AAV), such as described in U.S. Pat. No. 4,797,368 (Carter et al.) and in McLaughlin et al. (J. Virol. 62:1963-73, 1988) and AAV type 4 (Chiorini et al. J. Virol. 71:6823-33, 1997) and AAV type 5 (Chiorini et al. J. Virol. 73:1309-19, 1999), or retroviral vector (such as the Moloney murine leukemia virus, spleen necrosis virus, and vectors derived from retroviruses such as Rous sarcoma virus, Harvey sarcoma virus, avian leukosis virus, human immunodeficiency virus, myeloproliferative sarcoma virus, and mammary tumor virus). Other viral transfection systems may also be utilized, including vaccinia virus (Moss et al., 1987, Annu. Rev. Immunol. 5:305-24), bovine papilloma virus (Rasmussen et al., 1987, Methods Enzymol. 139:642-54) or members of the herpes virus group such as Epstein-Barr virus (Margolskee et al., 1988, Mol. Cell. Biol. 8:2837-47). In addition, vectors may contain antibiotic selectable markers (such as neomycin, hygromycin or mycophoenolic acid) to permit selection of transfected cells that exhibit stable, long-term expression of the vectors (and therefore the ZSCAN4 nucleic acid).

D. Nanoparticles for Delivery of ZSCAN4 Proteins and Nucleic Acids

Nanoparticles are submicron (less than about 1000 nm) sized drug delivery vehicles that can carry encapsulated drugs such as synthetic small molecules, proteins, peptides, cells and nucleic acid based biotherapeutics for either rapid or controlled release. A variety of molecules (e.g., proteins, peptides and nucleic acid molecules) can be efficiently encapsulated in nanoparticles using processes well known in the art.

The nanoparticles for use with the methods described herein can be any type of biocompatible nanoparticle, such as biodegradable nanoparticles, such as polymeric nanoparticles, including, but not limited to polyamide, polycarbonate, polyalkene, polyvinyl ethers, and cellulose ether nanoparticles. In some embodiments, the nanoparticles are made of biocompatible and biodegradable materials. In some embodiments, the nanoparticles include, but are not limited to nanoparticles comprising poly(lactic acid) or poly(glycolic acid), or both poly(lactic acid) and poly(glycolic acid). In particular embodiments, the nanoparticles are poly(D,L-lactic-co-glycolic acid) (PLGA) nanoparticles.

PLGA is a FDA-approved biomaterial that has been used as resorbable sutures and biodegradable implants. PLGA nanoparticles have also been used in drug delivery systems for a variety of drugs via numerous routes of administration including, but not limited to, subcutaneous, intravenous, ocular, oral and intramuscular. PLGA degrades into its monomer constituents, lactic and glycolic acid, which are natural byproducts of metabolism, making the material highly biocompatible. In addition, PLGA is commercially available as a clinical-grade material for synthesis of nanoparticles.

Other biodegradable polymeric materials are contemplated for use with the compositions and methods described herein, such as poly(lactic acid) (PLA) and polyglycolide (PGA). Additional useful nanoparticles include biodegradable poly(alkylcyanoacrylate) nanoparticles (Vauthier et al., Adv. Drug Del. Rev. 55: 519-48, 2003).

Among the biodegradable polymers currently being used for human applications, PLA, PGA, and PLGA are known to be generally safe because they undergo in vivo hydrolysis to harmless lactic acid and glycolic acid. These polymers have been used in making sutures when post-surgical removal is not required, and in formulating encapsulated leuprolide acetate, which has been approved by the FDA for human use (Langer and Mose, Science 249:1527, 1990); Gilding and Reed, Polymer 20:1459, 1979; Morris, et al., Vaccine 12:5, 1994). The degradation rates of these polymers vary with the glycolide/lactide ratio and molecular weight thereof. Therefore, the release of the encapsulated molecule (such as a protein or peptide) can be sustained over several months by adjusting the molecular weight and glycolide/lactide ratio of the polymer, as well as the particle size and coating thickness of the capsule formulation (Holland, et al., *J. Control. Rel.* 4:155, 1986).

In some embodiments, the nanoparticles for use with the compositions and methods described herein range in size from about 50 nm to about 1000 nm in diameter. In some cases, the nanoparticles are less than about 600 nm. In some embodiments, the nanoparticles are about 100 to about 600 nm in diameter. In some embodiments, the nanoparticles are about 200 to about 500 nm in diameter. In some embodiments, the nanoparticles are about 300 to about 450 nm in diameter. One skilled in the art would readily recognize that the size of the nanoparticle may vary depending upon the method of preparation, clinical application, and imaging substance used.

Various types of biodegradable and biocompatible nanoparticles, methods of making such nanoparticles, including PLGA nanoparticles, and methods of encapsulating a variety of compounds, including proteins and nucleic acids, has been well described in the art (see, for example, U.S. Publication No. 2007/0148074; U.S. Publication No. 20070092575; U.S. Patent Publication No. 2006/0246139; U.S. Pat. No. 5,753,234; U.S. Pat. No. 7,081,489; and PCT Publication No. WO/2006/052285).

The following examples are provided to illustrate certain particular features and/or embodiments. These examples should not be construed to limit the disclosure to the particular features or embodiments described.

EXAMPLES

Example 1: Materials and Methods

This example describes the experimental procedures used for the studies described in Example 2.

Subjects

Surgically resected pancreatic tissues and pancreatic biopsy samples were used for immunohistochemical analyses. Normal pancreatic tissues that were resected for the treatment of biliary carcinoma were used (n=3). Tissues resected for the treatment of chronic alcoholic pancreatitis (n=3) were also used. Pancreas biopsy samples from 18 patients with autoimmune pancreatitis were reported previously (Ko et al., *Gastroenterology* 138:1988-1996, 2010). All pancreatic biopsies were performed to exclude malignancy and written informed consent was obtained from each patient before the procedure. Under visual guidance of endoscopic ultrasonography (GF-UCT240, Olympus), pancreatic tissues were obtained from the body of the pancreas using a 19-gauge TRU-CUT™ biopsy needle (Wilson-Cook Inc.). Patients met the 2006 revised Japanese clinical diagnostic criteria for autoimmune pancreatitis: diffuse swelling of the pancreas, irregular narrowing of the main pancreatic duct, and a positive test for autoantibodies or a high IgG ($\geq$1800 mg/dl)/IgG4 concentration ($\geq$135 mg/dl). Among the 18 patients with autoimmune pancreatitis (Mizuno et al., *J Gastroenterol* 44:742-750, 2009), 3 patients were subjected to pancreatic biopsy to exclude malignancy at three different times: at the time of diagnosis, 3 months after the initiation of corticosteroid treatment, and 1 year after the start of treatment. A standard protocol for oral corticosteroids was used accordingly: prednisolone at 30 mg/day for a week as an initial dose, 20 mg/day for a second week, 10 mg/day for 4 additional weeks, and 5 mg/day as a maintenance dose all through the observation period (Ko et al., *Gastroenterology* 138:1988-1996, 2010).

Immunohistochemistry and Immunofluorescence

Both human and mouse pancreases were fixed in 10% formalin and embedded in paraffin. Embedded tissues were thin-sliced with a Leica microtome (Leica Microsystems GmbH, Wetzlar, Germany) at 5 mm. Sections were deparaffinized, permeabilized, and used for immunohistochemical analyses (Ko et al., *Gastroenterology* 138:1988-1996, 2010). Antibodies used in this study are summarized in Table 1.

TABLE 1

Antibodies Used For Immunohistochemical Analysis

| Antibodies | Species | Manufacturer | Product ID | Working Dilution | |
|---|---|---|---|---|---|
| Anti-aquaporin1 | Rabbit | ALPHA DIAGNOSTICS | AQP11-A | IHC<br>IF | 1:500<br>1:500 |
| Anti-amylase | Mouse | Abcam | ab54765 | IHC<br>IF | 1:300<br>1:100 |
| Anti-BMI1 | Mouse | MILLIPORE | 05-637 | IHC<br>IF | 1:200<br>1:100 |
| Anti-CFTR (#570) | Mouse | gift from Dr. Riordan (University of North Carolina) | | IHC<br>IF | 1:600<br>1:300 |
| Anti-CD163 | Mouse | Leica | NCL-CD163 | IHC<br>IF | 1:300<br>1:100 |
| Anti-ghrelin | Rabbit | Abcam | ab64325 | IHC<br>IF | 1:6000<br>1:1000 |
| | Mouse | Abcam | ab57222 | IHC<br>IF | 1:6000<br>1:1000 |
| Anti-glucagon | Rabbit | Abcam | ab18461 | IHC<br>IF | 1:5000<br>1:1000 |
| | Mouse | Abcam | ab10988 | IHC<br>IF | 1:4000<br>1:1000 |
| Anti-insulin | Guinea pig | Abcam | ab7842 | IHC<br>IF | 1:500<br>1:2000 |
| | Mouse | Abcam | ab7760 | IHC<br>IF | 1:3000<br>1:2000 |
| Anti-LGR5 | Rabbit | Abcam | ab75732 | IHC<br>IF | 1:300<br>1:100 |

TABLE 1-continued

Antibodies Used For Immunohistochemical Analysis

| Antibodies | Species | Manufacturer | Product ID | Working Dilution | |
|---|---|---|---|---|---|
| Anti-Somatostatin | Rat | Abcam | ab30788 | IHC | 1:1000 |
| | | | | IF | 1:500 |
| Anti-mZscan4 | Rabbit | NIA/NIH* | | IHC | 1:2000 |
| Anti-hZSCAN4 | Mouse | Abnova | H00201516-B01P | IHC | 1:200 |
| | | | | IF | 1:100 |

IHC, Immunohistochemistry; IF, Immunofluorescence
*Zalzman et al., Nature 464: 858-863, 2010

Antibodies were diluted according to the manufacturer's recommendation. Immunoreactions were intensified using Histofine Simple Stain MAX-PO (Nichirei Biosciences, Inc, Tokyo, Japan). Immunolabelling was visualized using 3,3'-diaminobenzidinetetrahydrochloride (DAB) as substrate for horseradish peroxidase. Sections were counterstained with Mayer's hematoxylin. For immunofluorescence, ALEXA FLUOR™ 488 (green) or ALEXA FLUOR™ 596 (red) labeled secondary antibodies were used for double staining. Immunolabelling was photographed with Olympus fluorescence microscopy (AX80; Olympus, Tokyo, Japan). Cell nuclei were counterstained with Hoechst 33342.

Materials

All the reagents in molecular biology grade were obtained from Sigma-Aldrich (St. Louis, Mo.) otherwise stated.

Example 2: Progenitor/Stem Cells Marked with ZSCAN4 in Adult Human Pancreas

This example describes the finding that a small number of ZSCAN4-positive cells are present among cells located in the islets of Langerhans, acini, and ducts of the adult pancreas. The results described in this example indicate that ZSCAN4 expression is a marker of rare stem/progenitor cells in the adult human pancreas.

Expression and Localization of ZSCAN4 in Adult Human Pancreas

Immunostaining with a specific antibody raised against human ZSCAN4 revealed that the majority of human pancreatic tissues were negative for ZSCAN4 staining, but a small number of cells showed strong nuclear staining for ZSCAN4 (FIG. 1A). More specifically, in the endocrine part of human pancreas, the majority of the islet of Langerhans did not show any ZSCAN4 staining, whereas some (<1%) of the islet of Langerhans showed ZSCAN4 staining; a few cells with strong nuclear staining and some of the remaining cells showed weak cytoplasmic staining (FIG. 1B). In the exocrine part of human pancreas, the majority of acinar cells did not show any ZSCAN4 staining, whereas some (<1%) acinar cells showed weak ZSCAN4 staining with occasional strong nuclear staining in a few cells (FIG. 1C). Furthermore, a small number of ZSCAN4-positive (ZSCAN4$^+$) cells were also found in pancreatic ducts (FIG. 1D). ZSCAN4 was also expressed in oval-shaped cells located in the region between pancreatic acini (FIG. 1E). From their location and cell morphology, these oval-shaped cells (tentatively called "pancreatic oval cells") can be identified as one form of pancreatic stellate cells (Bachem et al., Gastroenterology 115:421-432, 1998; Apte et al., Gut 43:128-133, 1998).

As validation for the human ZSCAN4 antibody, it was observed that both antibodies against human ZSCAN4 and mouse ZSCAN4 marked almost identical cells on either human (FIGS. 1F-1H and FIG. 1A-C) or mouse (FIGS. 6D-6L) pancreas sections. Because mouse ZSCAN4 is a specific marker for pluripotent ES cells (Falco et al., Dev Biol 307:539-550, 2007; Carter et al., Gene Expr Patterns 8:181-198, 2008) and is involved in genome stability in mouse ES cells (Zalzman et al., Nature 464:858-863, 2010), these immunohistological data indicate that ZSCAN4$^+$ cells are a good candidate for pancreatic tissue stem cells, which had been previously postulated, but not yet discovered (Aguayo-Mazzucato et al., Nat Rev Endocrinol 6:139-148, 2010).

Expression and Localization of LGR5 and BMI1 in Human Pancreas

To further investigate ZSCAN4$^+$ cells in the pancreas, two other proteins were selected that are well-established as tissue stem cell markers in mice: polycomb ring finger oncogene (BMI1) and leucine-rich repeat-containing G-protein-coupled receptor 5 (LGR5). BMI1 is necessary for efficient self-renewing cell divisions of adult mouse hematopoietic stem cells (Raaphorst, Trends Immunol 24:522-524, 2003). A single BMI1-expressing cell has been shown to form all the cell lineages in the intestinal epithelium (Ootani et al., Nat Med 15:701-706, 2009) and BMI1-lineage tracing has identified self-renewing pancreatic acinar cells capable of pancreatic organ homeostasis (Sangiorgi and Capecchi, Proc Natl Acad Sci USA 106:7101-7106, 2009). LGR5 is expressed in several organs (Barker and Clevers, Gastroenterology 138:1681-1696, 2010) and genetic marking of LGR5$^+$ cells has identified this membrane protein as a marker for intestinal and skin tissue stem cells in mice (Barker et al., Nature 449:1003-1007, 2007; Snippert et al., Science 327:1385-1389, 2010).

Figure 2:
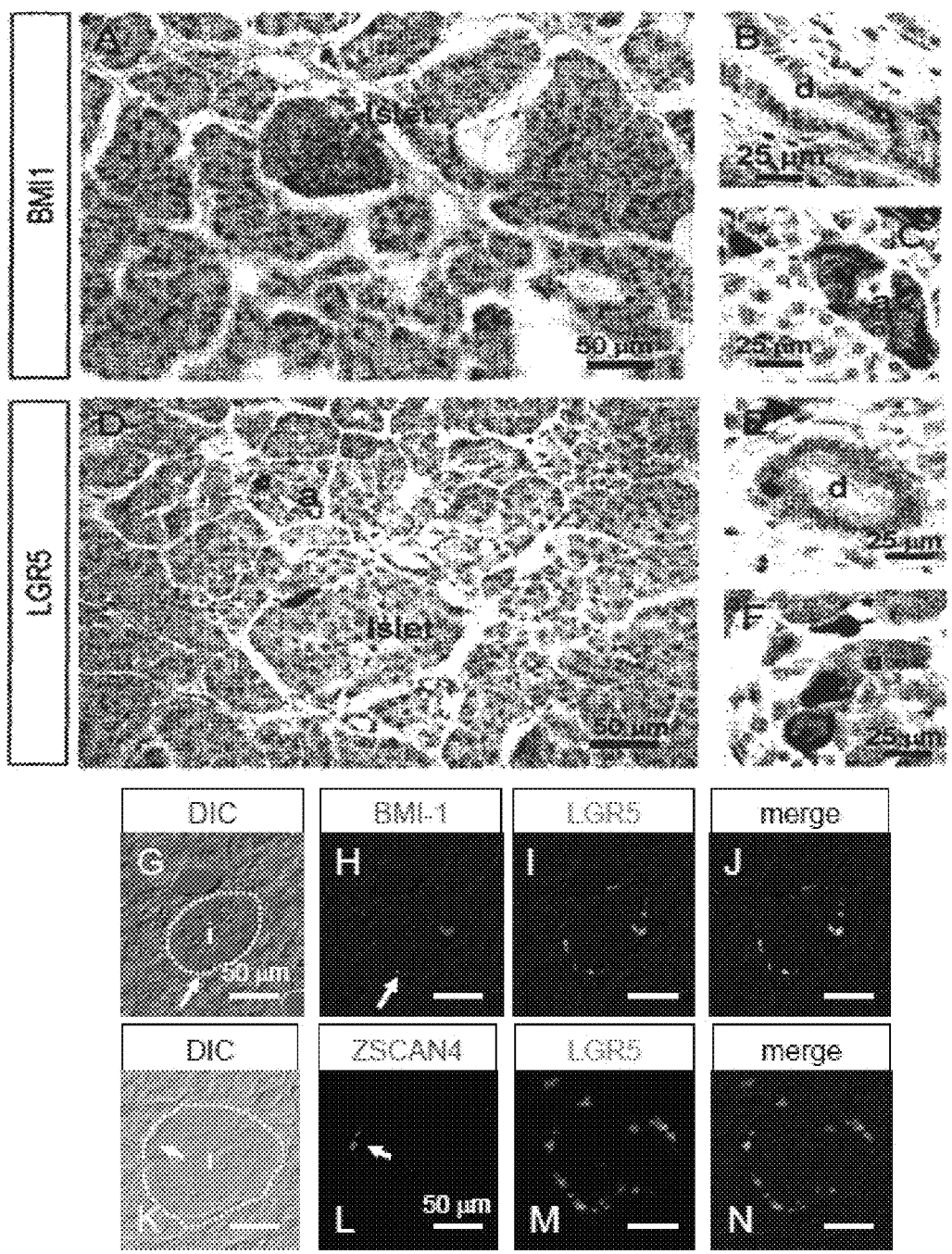
FIGS. 2A-2N are a series of images showing immunolocalization of BMI1 and LGR5 in human pancreas. BMI1+ cells are located in the islet of Langerhans (A), in the duct (B), and in acinus (C). LGR5+ cells are also localized in the islet of Langerhans (D), in the duct (E), and in acinus (F). Only a small number of cells are positive for BMI1 or LGR5, similar to the staining pattern of ZCAN4 in FIG. 1. Pancreatic oval cells between pancreatic acini are also positive for BMI1 and LGR5 (C and F). Double-immunofluorescent labeling of cells was performed in the islet of Langerhans (G-N). BMI1 and LGR5 mark identical cells in the islet (G-J). ZSCAN4 marks only a subset of LGR5 positive cells (K-N). d, duct; a, acinus; asterisk, oval cells; i, islet of Langerhans.
Figure 3:
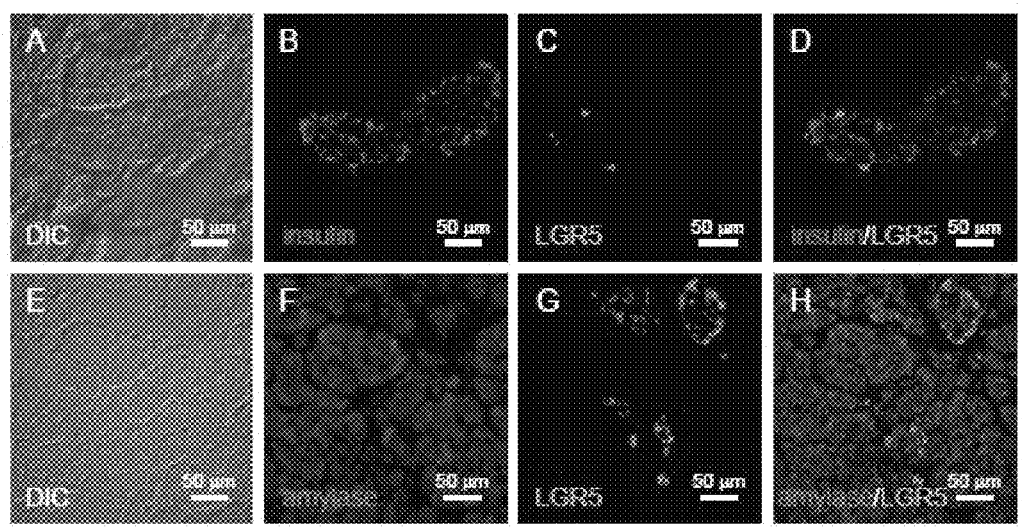
FIGS. 3A-3H are a series of images showing immunolocalization of insulin and LGR5 in a pancreatic islet (A-D). Insulin+ cells and LGR5+ cells are not co-localized. Immunolocalization of amylase and LGR5 in exocrine cells was performed (E-H). Amylase+ cells and LGR+ cells are not co-localized.

Immunohistochemical analyses showed that both BMI1 and LGR5 were detected in a small number of cells inside of the islets of Langerhans (FIG. 2A and FIG. 2D, respectively), duct cells (FIG. 2B and FIG. 2E, respectively), pancreatic acinar cells (FIG. 2C and FIG. 2D, respectively), and pancreatic oval cells located between adjacent acini (asterisks in FIG. 2C and FIG. 2F, respectively). Taken together, the localization of ZSCAN4$^+$, BMI1$^+$ and LGR5$^+$ cells were similar to each other; however, in general, BMI1$^+$ and LGR5$^+$ cells were more abundant than ZSCAN4$^+$ cells.

Presence of Cells Co-Stained with ZSCAN4, BMI1, and LGR5 in Human Pancreas

To examine if ZSCAN4, BMI1, and LGR5 are expressed in the same cells, double staining by immunofluorescence was performed in the same series of human paraffin sections. Cells expressing BMI1 and cells expressing LGR5 were mostly overlapped in human pancreatic sections, although slightly more LGR5$^+$ cells were noted than BMI1$^+$ cells (FIGS. 2G-2J). In contrast, ZSCAN4 expression was found only in a subset (5-10%) of LGR5$^+$ cells (FIG. 2K-2N). These results are in good agreement with the expression pattern of ZSCAN4 protein in mouse ES cells, where Zscan4 is transiently expressed and only about 5% of ES cells are positive for Zscan4 at a given time (Zalzman et al., *Nature* 464:858-863, 2010). The term "BMI1$^+$LGR5$^+$ZSCAN4$^{+\&-}$" is used to indicate the cells that are marked with the co-expression of BMI1 and LGR5 and have capacity to express ZSCAN4 intermittently.

Figure 4:
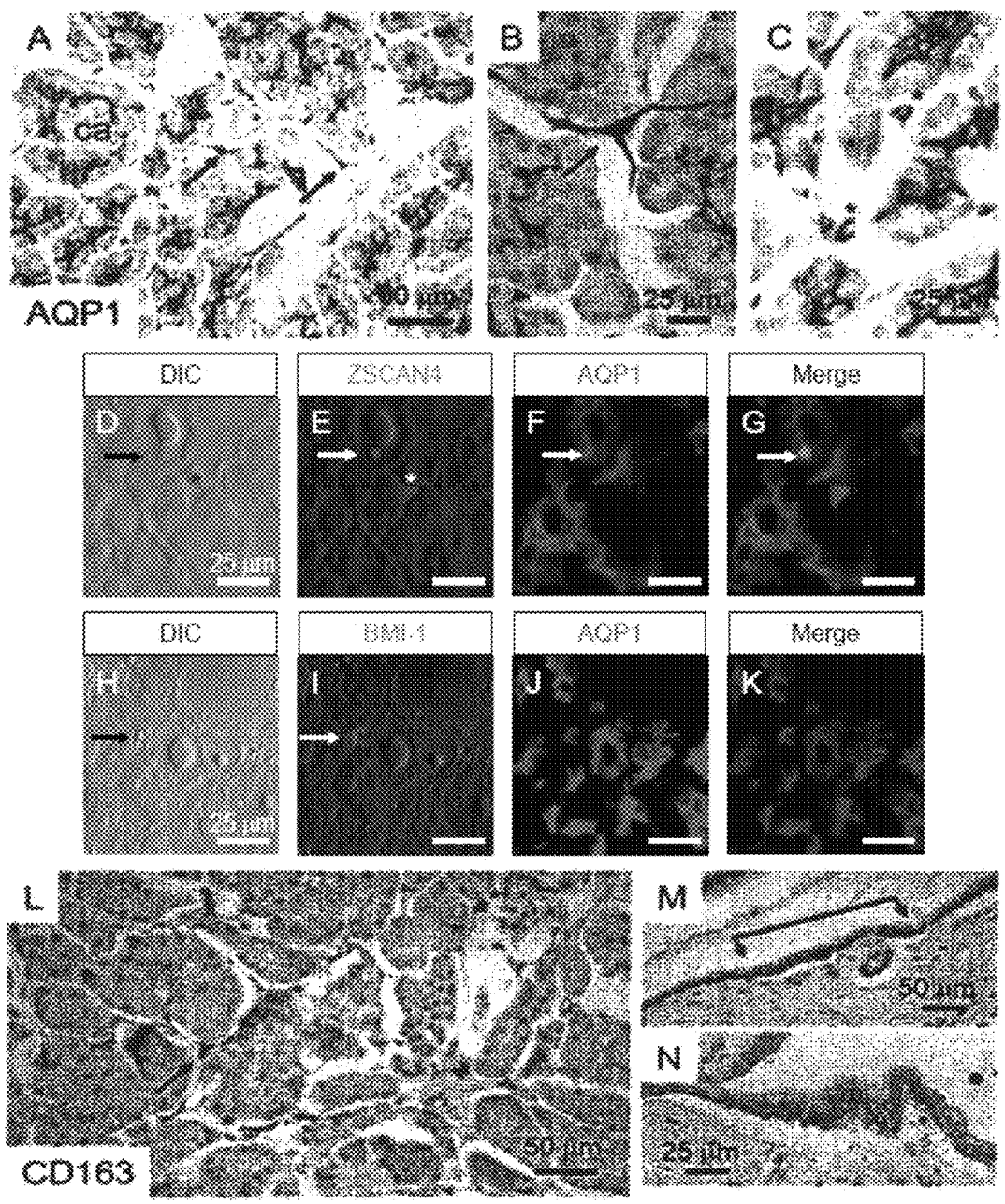
FIGS. 4A-4N are a series of images of human pancreas. (A-C) Immunolocalization of aquaporin 1 water channel (AQP1) in human pancreas. AQP1 is expressed in cells located from centroacinar cells (ca) to medium sized interlobular ducts. Both pancreatic stellate cells (black arrow) and oval cells (asterisk) are positive for AQP1. (D-G) A ZSCAN4+ cell in pancreatic duct is positive for AQP1. A rectangular-shaped ZSCAN4+ cell is AQP1 negative (asterisk). (H-K) BMI1+ cell is also positive for AQP1. BMI1+ cells are clearly distinguishable from neighboring cells by the DIC microscopy (H). (L-N) Localization of CD163+ cells. Most of the pancreatic stellate cells (arrow) and oval cells (asterisk) between acini are positive for CD163. A subset of pancreatic duct cells (M, between two black arrows) and basal membranes of pancreatic ducts (N) are also positive for CD163.

BMI1$^+$LGR5$^+$ZSCAN4$^{+\&-}$ Cells Express Neither Pancreatic Endocrine Hormones Nor Exocrine Enzyme Amylase were positive for the hematopoietic stem cell marker CD163 (FIG. 4L). It has been speculated that there is a connection between the pancreatic stellate cells and hematopoietic stem cells (Sparmann et al., *Cell Res* 20:288-298, 2010). Furthermore, some CD163$^+$ cells were also found in (FIG. 4M) and around pancreatic ducts, especially in the basal membrane near some pancreatic ducts (FIG. 4N). Immunohistochemical analyses are summarized in Table 2.

TABLE 2

Summary of immunohistochemical analyses

| Locations | Cell types | BMI1 | LGR5 | ZSCAN4 | Pancreatic hormones | Amylase | AQP1 | CFTR |
|---|---|---|---|---|---|---|---|---|
| Islet of Langerhans | BMI1$^+$LGR5$^+$ZSCAN4$^{+\&-}$ cells | + | + | +&− | − | − | − | − |
| | Other cells | − | − | − | + | − | − | − |
| Acinar | BMI1$^+$LGR5$^+$ZSCAN4$^{+\&-}$ cells | + | + | +&− | − | − | − | − |
| | Other cells | − | − | − | − | + | − | − |
| Duct | BMI1$^+$LGR5$^+$ZSCAN4$^{+\&-}$ cells | + | + | +&− | − | − | + | + |
| | Other cells | − | − | − | − | − | + | + |
| Other | Pancreatic oval cells | + | + | +&− | − | − | + | + |
| | Pancreatic stellate cells | − | − | − | − | − | + | − |

To examine if BMI1$^+$LGR5$^+$ZSCAN4$^{+\&-}$ cells have a phenotype of differentiated cells, fluorescence-based co-staining was carried out with the combination of an antibody against LGR5 and an antibody against one of the endocrine hormones or exocrine enzyme amylase.

Figure 9:
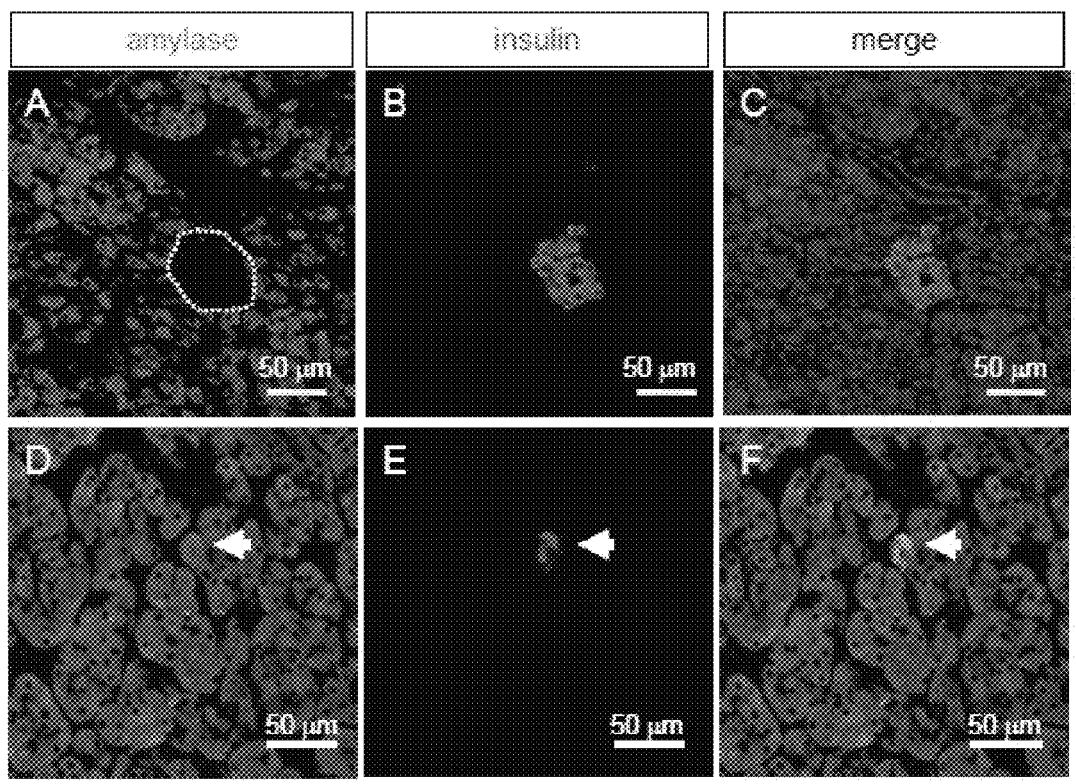
FIGS. 9A-9F are a series of images showing immunolocalization of insulin and amylase in human pancreas. (A-C) Exocrine cells produce digestive enzyme amylase and endocrine cells in the islet of Langerhans produce insulin. These cells are mutually exclusive in the pancreas. (D-F) A small number of cells in pancreatic acini are double-positive for insulin and amylase (arrow).

In pancreatic islets, LGR5$^+$ cells were all negative for insulin (FIGS. 3A-3D and FIGS. 8A-8C), glucagon (FIGS. 7A-7D and FIGS. 8D-8F), somatostatin (FIGS. 7E-7H and FIGS. 8G-8I), and ghrelin (FIGS. 7I-7L and FIGS. 8J-8L). Lack of expression of these endocrine hormones indicates that these BMI1$^+$LGR5$^+$ZSCAN4$^{+\&-}$ cells do not belong to known differentiated cells located in the islet of Langerhans, suggesting the presence of a novel cell type, possibly tissue stem/progenitor cells. A small number of endocrine hormones-expressing cells were also observed in pancreatic ducts (FIGS. 8C, 8F, 8I, and 8L) and pancreatic acini (FIGS. 8B, 8E, 8H, and 8K), which is consistent with previous reports (Bertelli and Bendayan, *Am J Physiol* 273:C1641-1649, 1997) (FIGS. 9D-9F).

In pancreatic acini, BMI1$^+$LGR5$^+$ZSCAN4$^{+\&-}$ cells were negative for digestive enzyme amylase—a specific marker for pancreatic exocrine cells (FIGS. 3E-3H), suggesting the presence of a novel cell type, possibly tissue stem/progenitor cells, in pancreatic acini.

Figure 5:
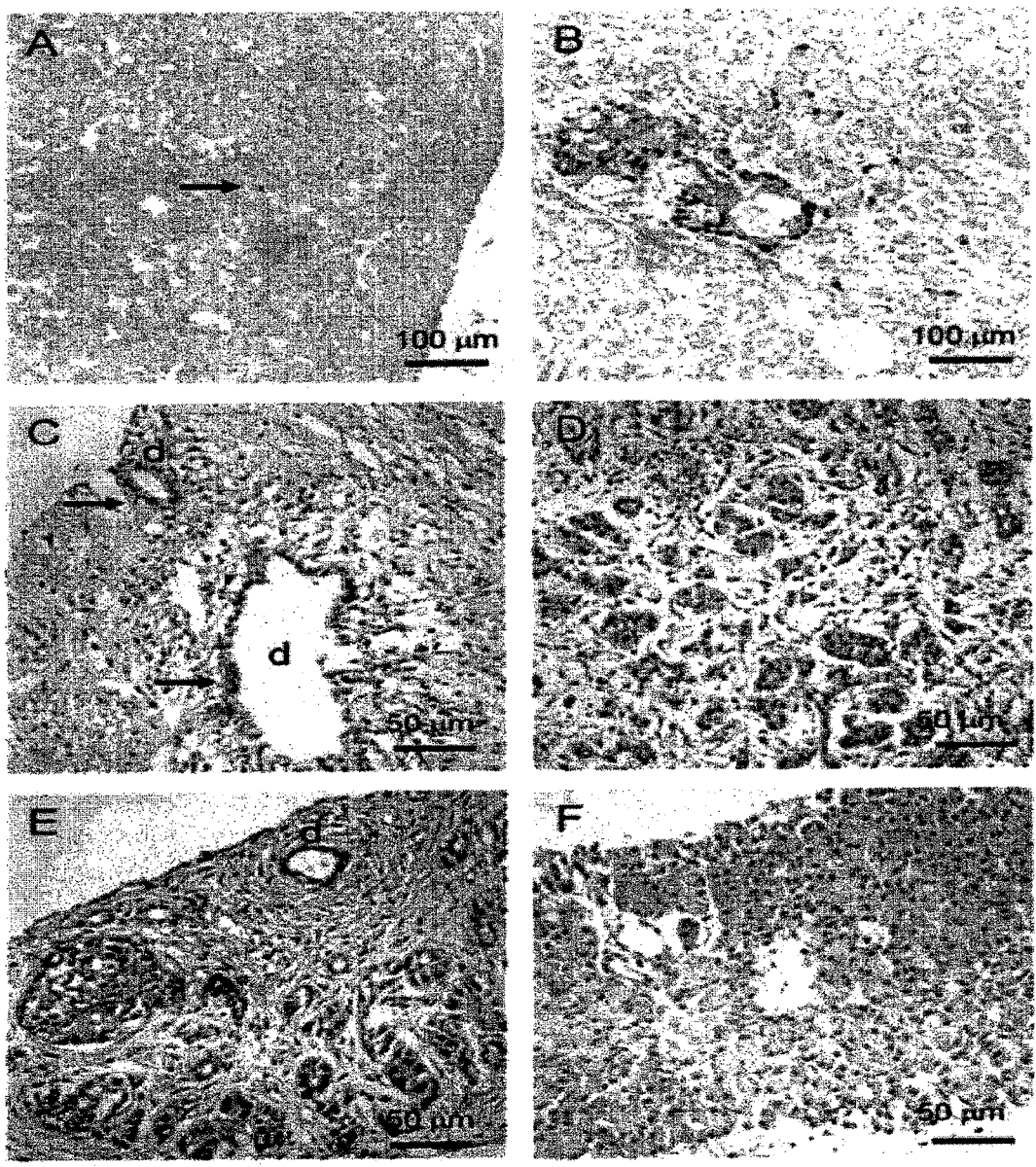
FIGS. 5A-5F are a series of images showing ZSCAN4 expression patterns in tissues taken from patients with chronic alcoholic pancreatitis and autoimmune pancreatitis. (A) A representative ZSCAN4-immunostaining of the pancreas from an unaffected individual (arrow, a ZSCAN4+ cell). (B) A representative ZSCAN4-immunostaining of the pancreas from a patient with chronic alcoholic pancreatitis. (C) A representative ZSCAN4-immunostaining of duct region of the pancreas from a patient with autoimmune pancreatitis before corticosteroid therapy. ZSCAN4+ cells increase in tissues on chronic inflammation (arrows, ZSCAN4+ cells). (D) A representative ZSCAN4-immunostaining of acinar region of the pancreas from a patient with autoimmune pancreatitis before corticosteroid therapy. (E) A representative ZSCAN4-immunostaining of the pancreas from a patient with autoimmune pancreatitis 3 months after the initiation of corticosteroid treatment. A large number of ZSCAN4+ cells are seen in pancreatic ducts, the islet of Langerhans, and regenerated acini. (F) A representative ZSCAN4-immunostaining of the pancreas from a patient with autoimmune pancreatitis 1 year after corticosteroids under the maintenance corticosteroid therapy. Only a few ZSCAN4+ cells are seen here. a, acinus; d, ducts; i, islet of Langerhans.
Figure 6:
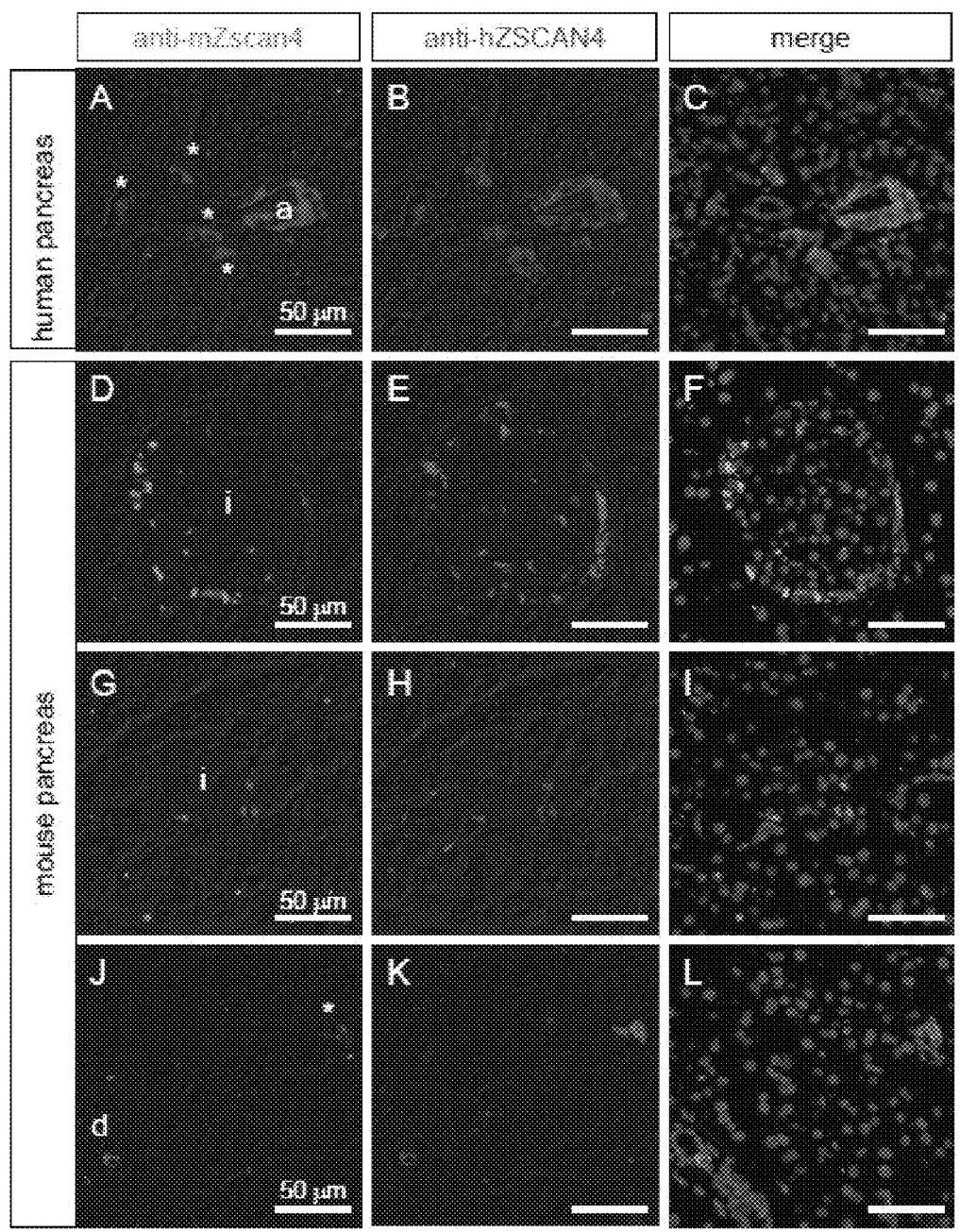
FIGS. 6A-6L are a series of images showing immunolocalization of ZSCAN4+ cells in mouse and human pancreas. An anti-mouse Zscan4 antibody (in A, D, G, and J) and anti-human ZSCAN4 antibody (in B, E, H, and K) mark identical cells both in human (C) and mouse pancreas (in F, I, and L).
Figure 7:
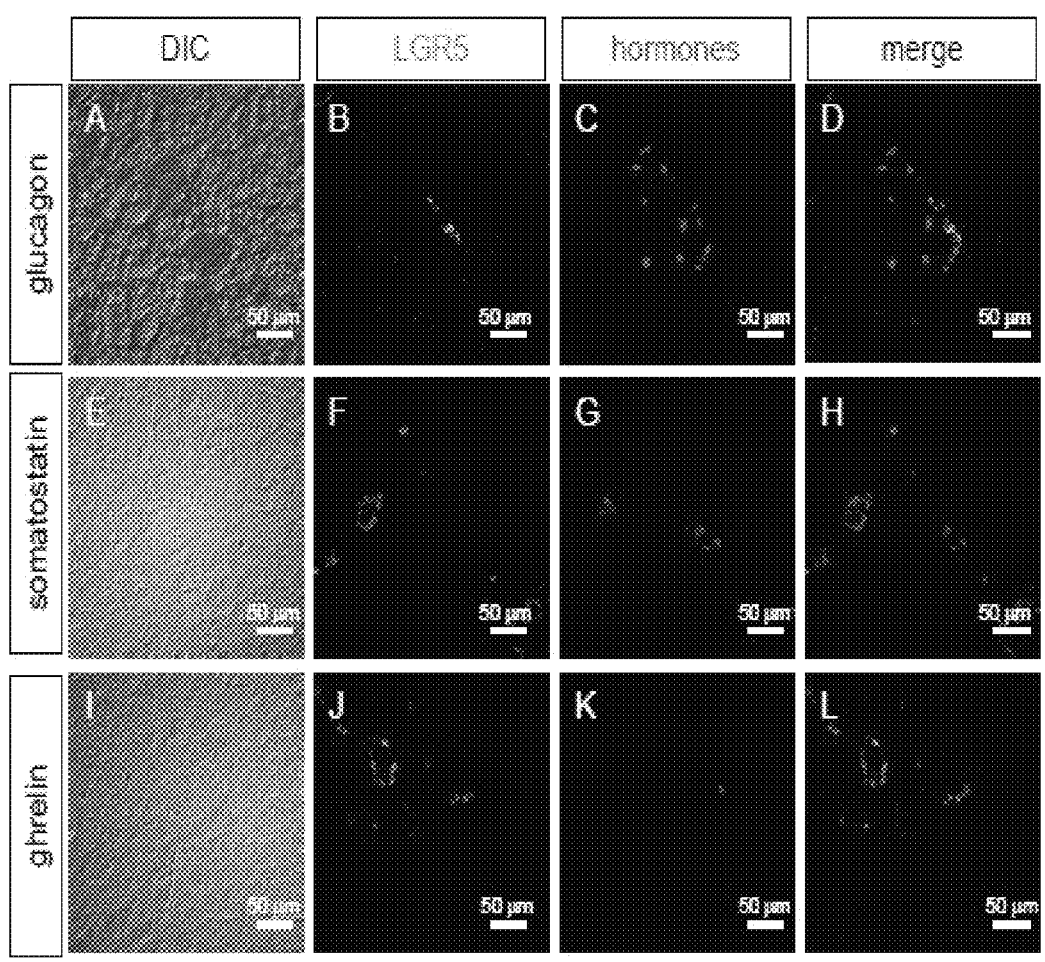
FIGS. 7A-7L are a series of images showing immunolocalization of pancreatic endocrine hormones and LGR5 in human pancreas. Shown is staining for glucagon (A-D), somatostatin (E-H), and ghrelin (1-L).
Figure 8:
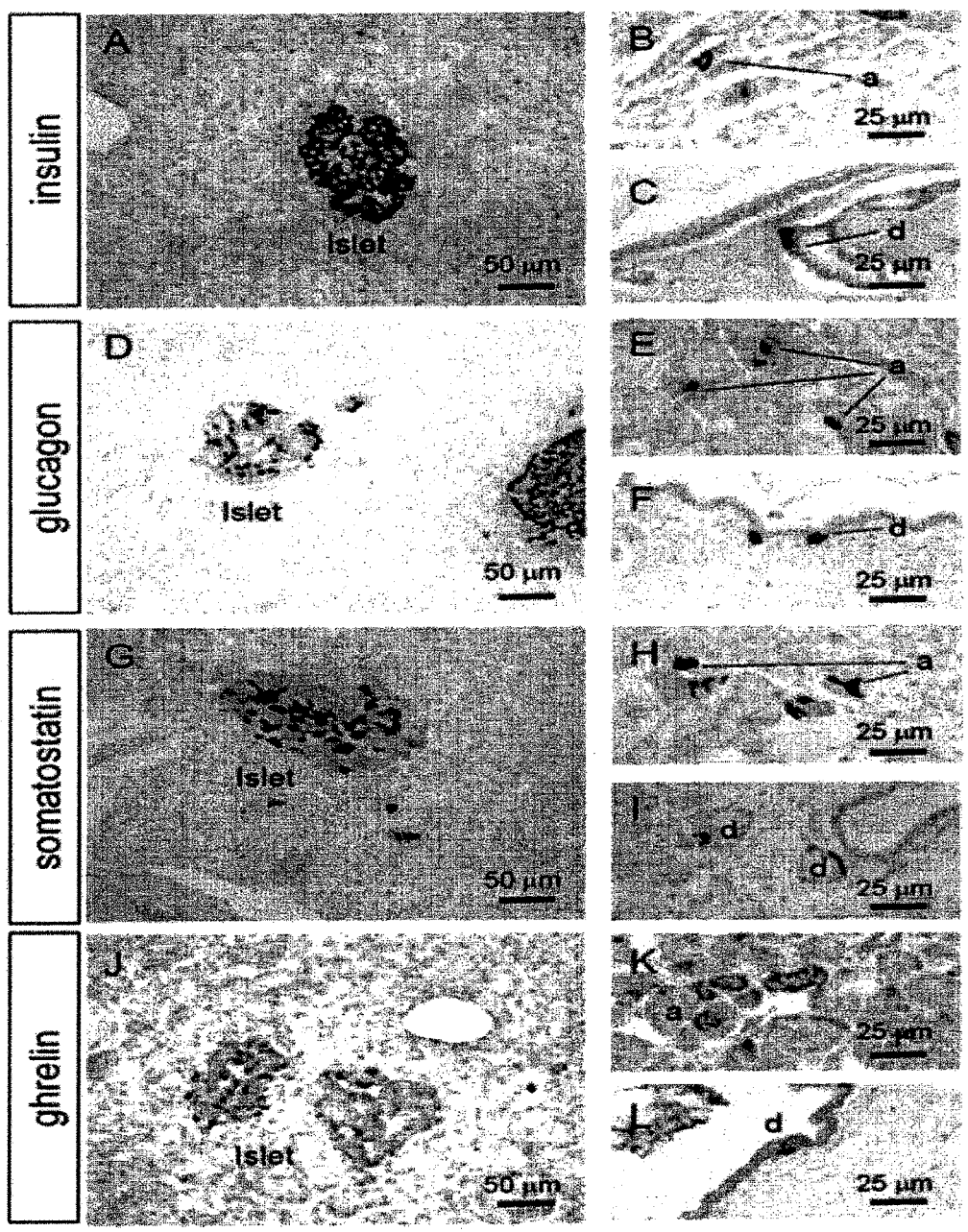
FIGS. 8A-8L are a series of images showing immunolocalization of endocrine hormones in human pancreas. Shown is staining for insulin (A-C), glucagon (D-F), somatostatin (G-I), and ghrelin (J-L). Endocrine hormone-positive cells are seen not only in pancreatic islets but also in pancreatic ducts (C, F, I, L), and pancreatic acini (B, E, H, K). a, acinus; d, duct.
Figure 10:
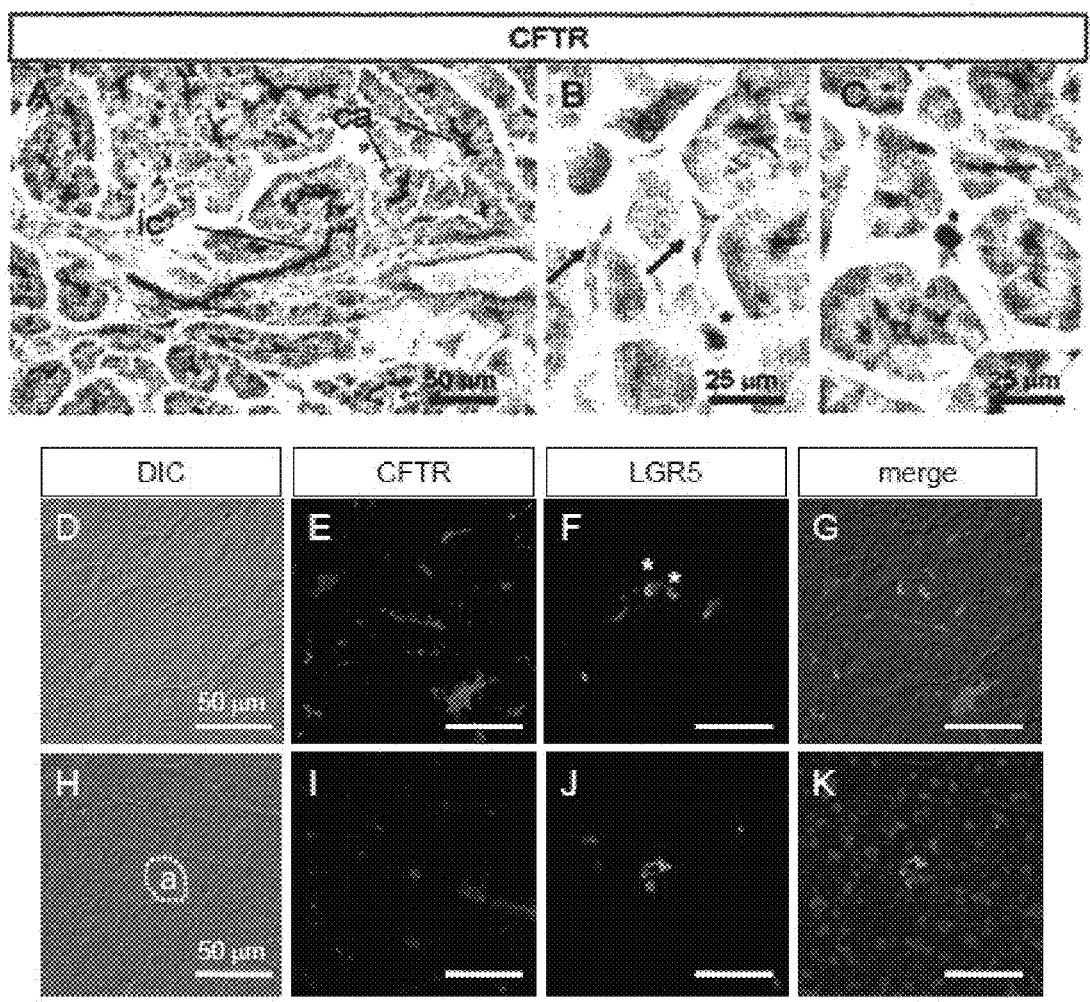
FIGS. 10A-10K are a series of images showing immunolocalization of cystic fibrosis transmembrane conductance regulator (CFTR) in human pancreas. CFTR is expressed in the apical plasma membrane of cells in small pancreatic ducts from centroacinar cells (ca) to intralobular ducts (A). By contrast to AQP1, CFTR is not expressed in pancreatic stellate cells (arrow) (B). However, pancreatic oval cells express CFTR in its plasma membrane (C). (D-H) Double-staining of cells with an anti-CFTR and anti-LGR5 antibody. CFTR and LGR5 expression are mutually exclusive (G and K). a, acinus; ic, intercalated duct; asterisk indicates pancreatic oval cells.

Expression of AQP1, CFTR, and CD163 in Some BMI1$^+$ $_{LGR}$5$^+$ZSCAN4$^{+\&-}$ Cells in Ducts and Interstitium Between Acini Both aquaporin 1 water channel (AQP1) and cystic fibrosis transmembrane conductance regulator (CFTR) chloride channel are expressed at the plasma membrane of human pancreatic ducts and can be used as markers for mature pancreatic duct cells (FIG. 4A and FIG. 10A) (Ko et al., *Gastroenterology* 138:1988-1996, 2010). In contrast to the cells in the islets and acini, a small number of BMI1$^+$LGR5$^+$ZSCAN4$^{+\&-}$ cells located in the pancreatic ducts were also positive for AQP1 (FIG. 4A and FIGS. 4D-4G). It was also found that the pancreatic stellate cells were positive for AQP1, but not for CFTR (FIGS. 4B and 4C). On the other hand, pancreatic oval cells were positive for both AQP1 and CFTR (FIG. 4C and FIGS. 10B and 10C). Most of the pancreatic oval cells as well as the pancreatic stellate cells Increase of ZSCAN4$^+$ Cells in Chronic Pancreatitis Next, ZSCAN4 expression was examined in the pancreatic tissues that were recovered from chronic inflammation after treating patients with corticosteroid hormone for three months (Ko et al., *Gastroenterology* 138:1988-1996, 2010). Compared to pancreatic tissues from an unaffected individual (FIG. 5A), a dramatic increase of the ZSCAN4$^+$ was observed in tissues under chronic inflammation: chronic alcoholic pancreatitis (FIG. 5B) and autoimmune pancreatitis (FIGS. 5C and 5D). Further increase of ZSCAN4$^+$ cells was observed in the pancreatic tissues regenerated after three-month corticosteroid treatment (FIG. 5E). As noted earlier, in the normal human pancreas, ZSCAN4$^+$ cells were very rare and rather difficult to spot (FIG. 5A); however, in the regenerated tissues ZSCAN4$^+$ cells were abundantly present (FIG. 5E). These ZSCAN4$^+$ cells disappeared and returned to a normal level one year after the treatment (FIG. 5F). These data indicate that the inflammation and regeneration of pancreatic tissues are accompanied with the increase of ZSCAN4$^+$ cells, suggesting the involvement of ZSCAN4$^+$ cells in the tissue regeneration.

Discussion

The immunohistochemistry analyses described above identified rare cells marked by the strong expression of ZSCAN4 as well as LGR5 and BMI1 in some of the islets, acini, ducts, and the interstitium between acini. These data indicate that these rare cells are tissue stem/progenitor cells in the adult human pancreas based on several lines of evidence.

First, coexpression of stem cell marker genes (ZSCAN4, LGR5, and BMI1) in these cells provides strong indication that these cells, though rare, are real and possess stem cell characters. Their infrequent presence in the pancreatic tissues is also consistent with the notion that the pancreas is an organ that does not have active tissue turnover/regeneration (Barker and Clevers, *Gastroenterology* 138:1681-1696, 2010). Furthermore, consistent with the strong expression of mouse Zscan4 in only about 5% of undifferentiated mouse ES cells at a given time (Zalzman et al., *Nature* 464:858-863, 2010), less than 10% of LGR5 positive cells are positive for ZSCAN4. This strong and unique pattern of ZSCAN4 expression in pancreas suggests the presence of functions similar to ES cells, i.e., a unique mechanism to maintain telomeres and genome stability in pancreas. The present disclosure provides the first demonstration of ZSCAN4 expression in human tissues and adult tissues/organs, as the inventors' previous study has shown the expression of mouse Zscan4 only in 2-cell embryos and a subpopulation of undifferentiated mouse ES cells (Falco et al., *Dev Biol* 307:539-550, 2007).

Second, the lack of differentiation markers, such as amylase and pancreatic hormones, in the BMI1$^+$LGR5$^+$ZSCAN4$^{+\&-}$ cells located among other differentiated cells in acini and islets strongly suggests that these cells are undifferentiated stem/progenitor cells. By contrast, BMI1$^+$LGR5$^+$ZSCAN4$^{+\&-}$ cells located in the pancreatic duct express AQP1 and CFTR, which are genes indicative of differentiation. This specific feature of BMI1$^+$LGR5$^+$ZSCAN4$^{+\&-}$ cells located in the duct may be related to the fact that the duct cells are often singled out as potential stem/progenitor cells in pancreas (Bonner-Weir et al., *Pediatr Diabetes* 5 Suppl 2:16-22, 2004).

Third, the number of ZSCAN4$^+$ cells dramatically increases in the pancreatic tissues being regenerated after corticosteroid therapy from the massive ablation of pancreatic acini due to the chronic inflammation, which is followed by the precipitous decrease to the normal level a year after the treatment. This suggests either the increase of ZSCAN4$^+$ tissue stem cell pools during pancreatic regeneration or the continued presence of ZSCAN4 proteins in the cells immediately after differentiation from ZSCAN4$^+$ putative tissue stem cells. Observation of the significant increase of ZSCAN4$^+$ in chronic pancreatitis suggests the role of pancreatic stem/progenitor cells in regeneration of pancreatic parenchyma by immunosuppressive therapy on inflammation.

Fourth, BMI1$^+$LGR5$^+$ZSCAN4$^{+\&-}$ cells are also located between adjacent pancreatic acini or around pancreatic ducts. Based on their location and the expression of AQP1 and hematopoietic stem cell marker CD163, these oval-shaped BMI1$^+$LGR5$^+$ZSCAN4$^{+\&-}$ cells may be related to the pancreatic stellate cells (Apte et al., *Gut* 43:128-133, 1998), which are thought to be involved in pancreas fibrosis on chronic inflammation (Masamune et al., *Clin Gastroenterol Hepatol* 7:S48-54, 2009) and at least some of which are thought to be bone marrow derived stem/progenitor cells (Sparmann et al., *Cell Res* 20:288-298, 2010; Marrache et al., *Gut* 57:1113-1120, 2008). Recent demonstration that some of the pancreatic stellate cells are progenitor cells that can produce β like cells (Mato et al., *Biochem J* 421:181-191, 2009) may suggest that these cells are overlapped with the oval-shaped BMI1$^+$LGR5$^+$ZSCAN4$^{+\&-}$ cells located in the place for the pancreatic stellate cells.

Type 1 diabetes and a subset of type 2 diabetes occur when there is an inadequate functional mass of insulin-producing pancreatic β cells. Diabetes could be cured if it were possible to find a way to obtain enough β cells for cell replacement therapy. Although cadaver islets, human ES cells, and induced pluripotent stem (iPS) cells are believed to be good candidates for the source of β cells for transplantation (Bonner-Weir and Weir, *Nat Biotechnol* 23:857-861, 2005), there are major obstacles to overcome before successful β cell replacement therapy is available. The pancreatic stem/progenitor cells disclosed herein could serve as a new source of differentiated β cells, as it is possible to obtain small pieces of pancreatic tissues by ultrasound guided TRU-CUT™ biopsy (Mizuno et al., *J Gastroenterol* 44:742-750, 2009).

Example 3: Co-Expression of ZSCAN4 and Stem Cell Marker SSEA3

Figure 11:
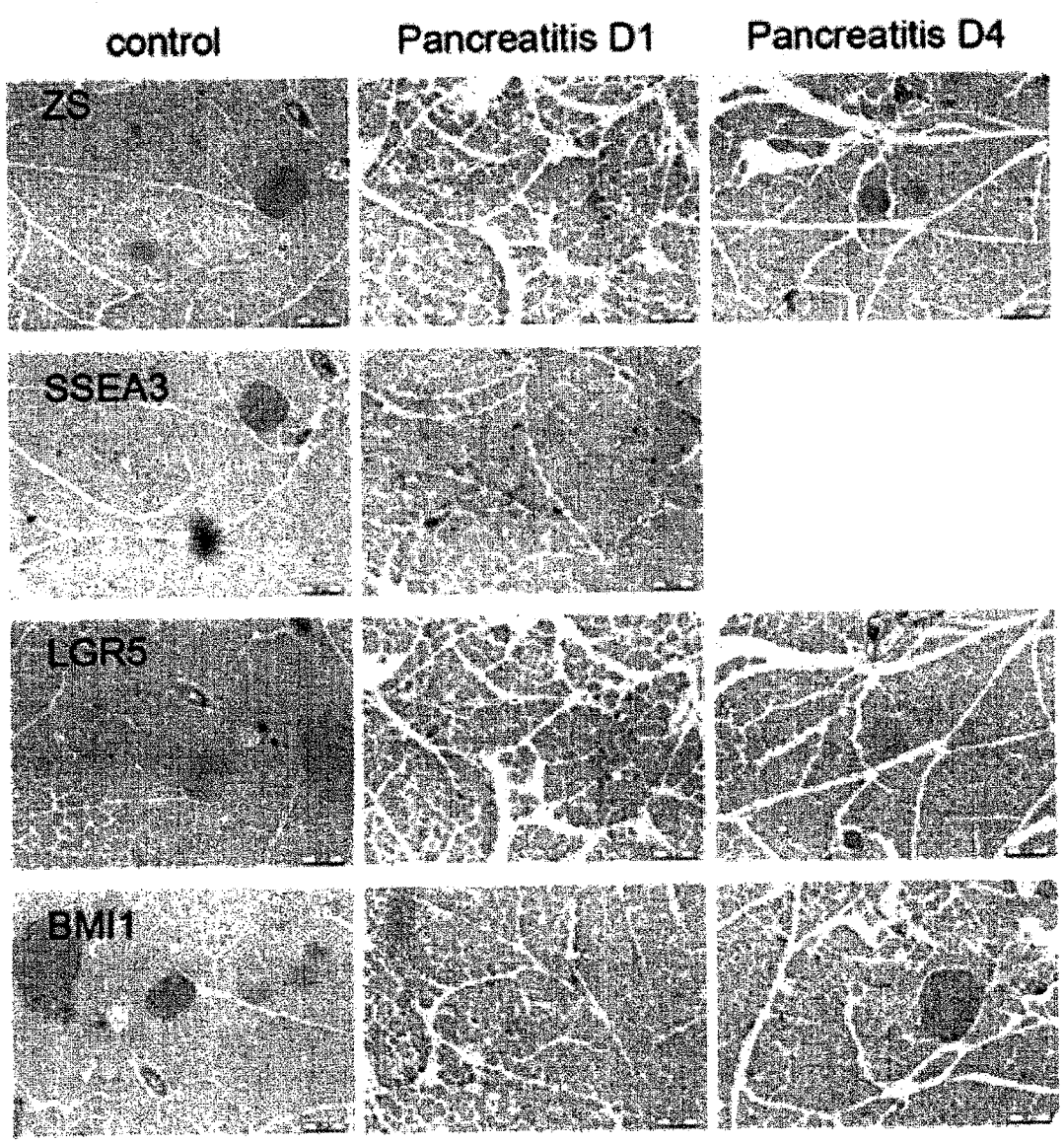
FIG. 11 is a series of images showing immunohistochemical staining of mouse pancreatic tissue to detect expression of Zscan4, SSEA3, LGR5 and BMI1. Shown are tissue sections from control animals and animals with caerulein-induced pancreatitis (D1: 1 day after caerulein treatment; D4, 4 days after caerulein treatment).

Caerulein-induced experimental pancreatitis has been widely used as a model for pancreatitis. Expression patterns of ZSCAN4 and other markers, including stage-specific embryonic antigen-3 (SSEA3), a carbohydrate epitope and a known stem cell marker, were examined in pancreatic tissues undergoing pancreatitis. Immunohistochemical staining was performed to evaluate expression of Zscan4, SSEA3, LGR5 and BMI1. As shown in FIG. 11, SSEA3 exhibits a similar (but not identical) expression pattern as Zscan4. Thus, these results indicate that SSEA3 can be used in some instances as a marker for ZSCAN4-expressing cells and/or as a means of enriching ZSCAN4$^+$ cells.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

The invention claimed is:

1. A method of isolating pancreatic stem cells, pancreatic progenitor cells, or pancreatic stem cells and pancreatic progenitor cells that express a zinc finger and SCAN domain containing protein 4 (ZSCAN4 protein) from a sample comprising pancreatic tissue, the method comprising:
   (i) detecting expression of the ZSCAN4 protein, an mRNA encoding the ZSCAN4 protein, an SSEA3 protein, an mRNA encoding the SSEA3 protein, a Tcstv1/3 protein, or an mRNA encoding the Tcstv1/3 protein in cells of the sample; and
   (ii) isolating the cells that express the ZSCAN4 protein, the mRNA encoding the ZSCAN4 protein, the SSEA3 protein, the mRNA encoding the SSEQA3 protein, the Tcstv1/3 protein or an mRNA encoding the Tcstv1/3 protein, thereby isolating pancreatic stem cells, pancreatic progenitor cells, or pancreatic stem cells and pancreatic progenitor cells from the sample.

2. The method of claim 1, wherein detecting expression of the ZSCAN4 protein comprises contacting the sample with an antibody specific for the ZSCAN4 protein.

3. The method of claim 1, wherein detecting expression of the mRNA encoding the ZSCAN4 protein is by PCR.

4. The method of claim 1, wherein detecting expression of the SSEA3 protein or the Tcstv1/3 protein comprises contacting the sample with an antibody specific for the SSEA3 protein or the Tcstv1/3 protein, respectively.

5. The method of claim 4, wherein the antibody is specific for the SSEA3 protein.

6. The method of claim 4, wherein the antibody is specific for the Tcstv1/3 protein.

7. The method of claim 1, wherein detecting expression of ZSCAN4 comprises transfecting the cells of the sample with a vector comprising a ZSCAN4 promoter operably linked to a reporter gene or a selectable marker.

8. The method of claim 7, wherein the ZSCAN4 promoter is a mouse Zscan4c promoter.

9. The method of claim 8, wherein the Zscan4c promoter comprises the nucleic acid sequence set forth as nucleotides 906-4468 of SEQ ID NO: 15.

10. The method of claim 7, wherein the reporter gene encodes a fluorescent protein.

11. The method of claim 10, wherein the fluorescent protein is a green fluorescent protein, or a variant thereof.

12. The method of claim 7, wherein the vector comprises the nucleic acid sequence set forth as SEQ ID NO: 15.

13. The method of claim 7, wherein the selectable marker is an antibiotic resistance gene.

14. The method of claim 13, wherein the antibiotic resistance gene is a puromycin-resistance gene.

15. The method of claim 1, wherein the sample comprises human pancreatic tissue obtained by biopsy.

16. The method of claim 1, wherein the method further comprises detecting expression of LGR5 or BMI1, or both, in cells of the sample, and isolating cells that also express LGR5 or BMI1, or both.

* * * * *